(12) United States Patent
Abel et al.

(10) Patent No.: US 9,585,550 B2
(45) Date of Patent: Mar. 7, 2017

(54) RECTAL EXPANDER

(75) Inventors: Eric Abel, Dundee (GB); James R. Hewit, Dundee (GB); Alan P. Slade, Dundee (GB); Zhigang Wang, Dundee (GB)

(73) Assignee: University of Dundee, Dundee (GB)

( * ) Notice: Subject to any disclaimer, the term of this patent is extended or adjusted under 35 U.S.C. 154(b) by 2348 days.

(21) Appl. No.: 10/561,649

(22) PCT Filed: Jun. 24, 2004

(86) PCT No.: PCT/GB2004/002695
§ 371 (c)(1),
(2), (4) Date: Mar. 21, 2007

(87) PCT Pub. No.: WO2005/000111
PCT Pub. Date: Jan. 6, 2005

(65) Prior Publication Data
US 2007/0276189 A1 Nov. 29, 2007

(30) Foreign Application Priority Data
Jun. 26, 2003 (GB) .................................. 0314863.2

(51) Int. Cl.
  *A61M 29/00* (2006.01)
  *A61B 1/32* (2006.01)
  *A61B 1/31* (2006.01)
(52) U.S. Cl.
  CPC .................. *A61B 1/32* (2013.01); *A61B 1/31* (2013.01); *A61M 29/00* (2013.01)

(58) Field of Classification Search
  USPC ........ 606/198, 110–114, 127, 128, 159, 197, 606/21, 47, 190, 199; 604/104–109; 600/201–206, 184, 210–215, 235
  See application file for complete search history.

(56) References Cited

U.S. PATENT DOCUMENTS

| | | | | |
|---|---|---|---|---|
| 1,267,066 A * | 5/1918 | Flack | ............................ | 606/197 |
| 5,325,848 A * | 7/1994 | Adams et al. | ................ | 600/206 |
| 5,454,365 A * | 10/1995 | Bonutti | ......................... | 600/204 |
| 5,678,572 A * | 10/1997 | Shaw et al. | ................... | 128/899 |
| 5,797,907 A * | 8/1998 | Clement | ......................... | 606/49 |
| 6,443,959 B1 * | 9/2002 | Beland et al. | ................ | 606/127 |
| 6,656,154 B1 * | 12/2003 | Addis | ....................... | 604/100.01 |
| 6,673,070 B2 * | 1/2004 | Edwards et al. | ................ | 606/41 |
| 7,048,734 B1 * | 5/2006 | Fleischman et al. | ........... | 606/42 |
| 7,198,626 B2 * | 4/2007 | Lee et al. | ........................ | 606/47 |
| 2002/0013601 A1 * | 1/2002 | Nobles et al. | ................ | 606/193 |
| 2002/0111639 A1 * | 8/2002 | Armstrong | .................... | 606/144 |

* cited by examiner

*Primary Examiner* — Elizabeth Houston
*Assistant Examiner* — Lindsey Bachman
(74) *Attorney, Agent, or Firm* — Dinsmore & Shohl LLP

(57) ABSTRACT

There is disclosed medical apparatus of the type for use in surgery such as transanal endoscopic microsurgery, as well as methods of providing access to, inspecting and enabling surgery within a body passage. In one embodiment of the invention, medical apparatus in the form of a rectal expander (10) is disclosed, the expander (10) being adapted for location at least partly within a body passage such as the rectum (12) of a patient (14), the expander (10) having a leading end (18) and an access area in the form of an opening (20) for access from the expander (10) into the rectum (12), at least part of the opening (20) being spaced from the leading end (18), and the expander (10) being controllably movable between collapse and expansion positions, for expanding the rectum (12).

35 Claims, 22 Drawing Sheets

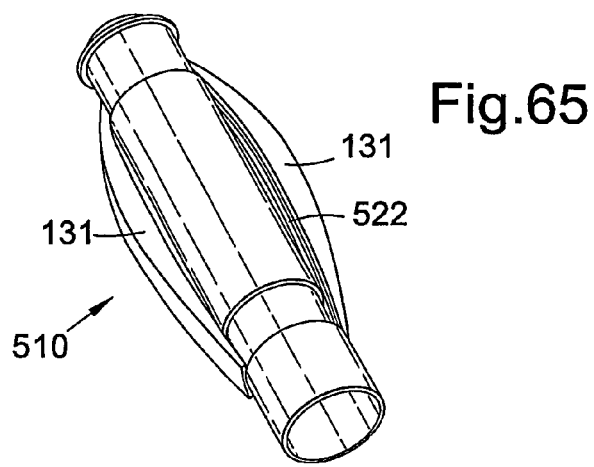
Fig.65
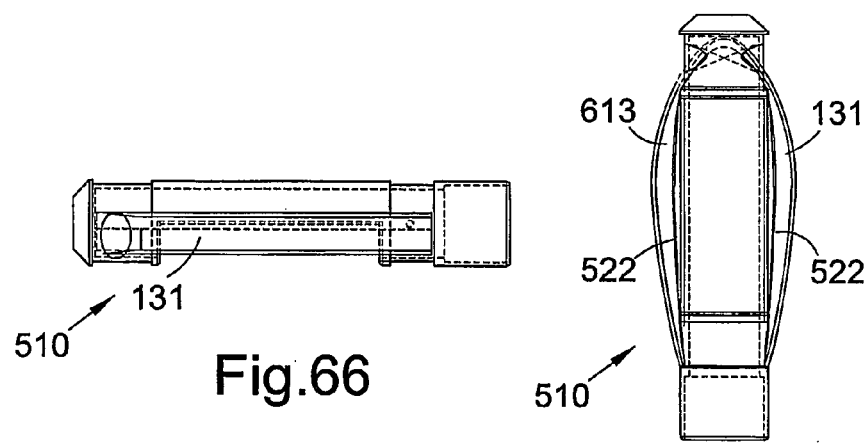
Fig.66
Fig.67
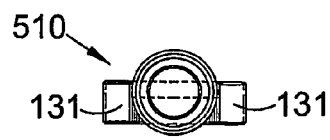
Fig.68

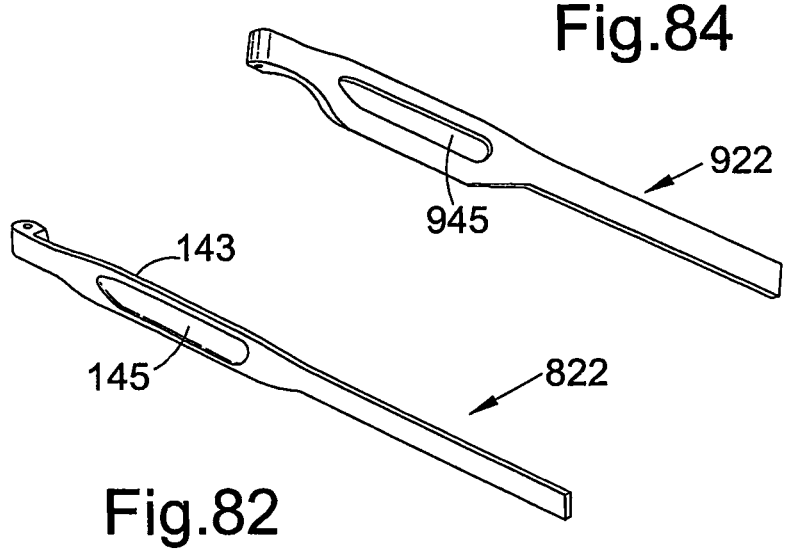
Fig.84
Fig.82
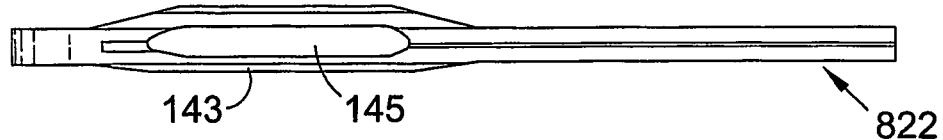
Fig.83

RECTAL EXPANDER

FIELD OF THE INVENTION

The present invention relates to medical apparatus and to methods of providing access to, inspecting and enabling surgery within a body passage. In particular, but not exclusively, the present invention relates to medical apparatus of the type for use in surgery such as transanal endoscopic microsurgery.

BACKGROUD OF THE INVENTION

Transanal endoscopic microsurgery (TEM) is used to treat lesions within the rectum. Existing TEM equipment, as described by Buess et al, comprises a long rigid tube which is inserted through the anus. Long slender instruments, including an endoscope, are deployed through this tube to perform operations within the rectal cavity, which is insufflated with $CO_2$ gas. This requires the tube to be equipped with seals to prevent loss of insufflation, which in turn requires the use of glands through which the instruments are passed. The seals and glands, together with the length and narrowness of the tube, make it very awkward for a surgeon to use the instruments. Furthermore, the seals and glands prevent the surgeon from obtaining much useful force and tactile feedback, which can lead to surgical errors being made, and existing TEM equipment is very expensive. These problems have militated against TEM becoming a popular procedure.

Alternative proposals are based upon mechanical exposure and/or expansion of the rectum. For example, Yamashita et al discloses a front lifting hood rectoscope tube for TEM, which mainly comprises a long rectoscope tube. The forward half of the tube is opened longitudinally by hand, by rotating an external control screw, to expand the mouth of the tube from 40 mm up to 70 mm in diameter (or by up to a 25° lifting angle). However, the surgical site or lesions must be located beyond the far end of the rigid tube and are accessed through the mouth of the tube. This is essentially the same as the Buess et al proposal. Therefore, access to the lesions is still restricted by the long rigid tube and the relatively small opening at the far end (normally providing an access angle of less than 15°, or a maximal access angle of 25° in a vertical plane after opening).

The improved exposure provided by $CO_2$ gas insufflation is one of the key features which sets the Buess et al proposal apart from conventional instrumentation. The mechanical expansion/exposure afforded by Yamashita is not sufficient given its maximal opening of 70 mm diameter at the far end. Also, the rectal walls (lumen) beyond the far end are not supported and liable to collapse. Indeed, Yamashita proposes using positive air insufflation first to locate and expose the lesion, viewing through a sealed glass window attached to the proximal end. The rectum is then deflated, the tube opening out, and the operation is carried out gasless under endoscopic visualization.

Kakizoe et al discloses a rectal expander made of a clear polyethylene, essentially a modified plastic beverage bottle having two legs. The diameter of the rectal expander in a folded position, where the two plastic legs and the bottom half of the plastic bottle at the proximal end are folded, is around 30 mm. This becomes around 58 mm after expanding the rectum by un-folding the two legs and the bottle.

There are many disadvantages to the Kakizoe proposal. These include that un-folding the expander can easily cause rectal tissue tear, as happened in one of their three disclosed examples, due to lack of control of the folding and un-folding procedure. Also, the expander has a fixed expanded size of 58 mm diameter only in the area of the legs, which is not sufficient for larger tumours. The plastic legs also have to be strong enough to support rectal expansion, and it was discovered that wider legs are needed. However, the un-folded wider legs further limit the size of the surgical site, which needs a clearance away from the un-folded legs. Additionally, due to lack of support or expansion at higher, distal ends, the device cannot be used to access or excise tumours at a high location (far along the rectum).

Kanehira et al discloses results of endorectal surgery using a rectal tube with a side window. The rectal tube, made of transparent plastic, measures around 40 mm in diameter and 150 mm in insert length. The tube is tapered and closed at the forward tip and has a round window on its side. The centre of the side window is 100 mm along the tube, and is intended to entrap the target lesion, so that a surgical procedure can be performed inside the tube. A stated aim is to solve the problem of poor visualisation of a target lesion when it is hidden behind a Houston's valve (located between the transverse and descending sections of the colon in front of the position of the left kidney). In conventional TEM this situation cannot be simply improved.

Disadvantages with the Kanehira et al device include its fixed window location; there is no mechanical expansion apart from that caused by insertion of the tube itself (40 mm in diameter); and there is a risk of damaging normal tissue or fragmenting a corner of a tumour by the rim of the side window, especially during rotating or sliding for excising tumours larger than 40 mm in diameter. The reference discusses the fact that although it is possible to produce a tube with a larger window, such a tube would not be physically tough enough, and could break in the rectal cavity.

In summary, poor functionality and problems associated with $CO_2$ gas insufflation, together with the high cost of equipment and special training required for surgeons, have prevented conventional and existing TEM from becoming a popular procedure in the treatment of early rectal cancer. The gasless, mechanical TEM proposals discussed above are deficient in that they do not allow a surgeon to sufficiently visualize the surgical site with good lumen support/expansion, nor to access tumours ranging from low to high positions within the rectum.

It is amongst the objects of embodiments of the present invention to obviate or mitigate at least one of the foregoing disadvantages.

SUMMARY OF THE INVENTION

According to a first aspect of the present invention, there is provided medical apparatus adapted for location at least partly within a body passage, the apparatus having a leading end and an area for access from the apparatus into the body passage, at least part of the area spaced from the leading end, and the apparatus being controllably movable between collapse and expansion positions, for expanding the body passage.

It will be understood that the access area allows viewing, inspection, diagnostic and surgical procedures to be conducted.

Preferably, the apparatus is adapted to be located within the body passage in the collapse position, and subsequently moved to the expansion position. This facilitates insertion and location of the apparatus within the body passage, and allows removal by returning the apparatus to the collapse position.

The ability of the apparatus to be controllably moved between the collapse and expansion positions allows progressive movement between the respective positions. This helps prevent accidental injury during expansion or collapse of the apparatus. Furthermore, this allows the apparatus to be moved to a position between the collapse and expansion positions. For example, an operator may determine that it is not required or appropriate to expand the apparatus (and thus the body passage) to a fully expanded position, and may instead determine that a position intermediate the full collapse and expansion positions may be sufficient.

Preferably, the apparatus is an expander, typically a rectal expander for use in TEM. Alternatively, the apparatus may be suitable for use in gynaecological procedures.

The access area may facilitate access to the body passage from the apparatus. In particular, the provision of an access area with at least part spaced from the leading end of the apparatus allows improved access and manoeuvrability of surgical tools and the like inserted into the body passage, when compared to prior proposals.

Preferably, the collapse position of the apparatus comprises a rest position and the expansion position a stressed position. The apparatus may therefore be adapted to move to the collapse position in the absence of an applied expansion force. Alternatively, the collapse position may comprise a stressed position and the expansion position a further stressed position. In a further alternative, the collapse position may comprise a stressed position and the expansion position a rest position. Accordingly, the apparatus may be adapted to move to the expansion position in the absence of an applied collapse force.

The apparatus may comprise an actuating device for moving the apparatus between the collapse and expansion positions. The actuating device may comprise an activating member moveable relative to a remainder of the apparatus for moving the apparatus between the collapse and expansion positions. The actuating device may comprise a mechanical, electromechanical, electrical, electronic, pneumatic or hydraulic device, or a combination thereof.

Preferably, the actuating device comprises a screw mechanism which may include a screw threaded member coupled to the activating member, rotation of the screw threaded member causing a movement of the activating member relative to a remainder of the apparatus, thereby moving the apparatus between the collapse and expansion positions. In an alternative embodiment, the actuating device may comprise a ratchet mechanism, where the activating member is moved manually or otherwise.

The actuating device may comprise a motor such as an electrical or hydraulic motor, which may be provided as part of a screw mechanism or linear actuator for moving the activating member. Alternatively, the apparatus may comprise an inflatable element and a pump.

The apparatus may comprise a lock for locking the apparatus in a desired position, which may comprise the collapse position, the expansion position or a position therebetween. Preferably, the lock forms part of the actuating device. For example, where the actuating device comprises a screw threaded or ratchet mechanism, the mechanism may be self-locking or may be locked by a lock member.

Preferably, the apparatus comprises a guide member adapted for location at least partly within the body passage. The guide member may define the leading end and the access area of the apparatus. The apparatus may comprise a hollow guide member, a wall of the guide member defining the access area. The access area may comprise an opening in the guide member, and may comprise an aperture in the wall of the guide member. A distance between the opening and a trailing end of the guide member may be minimised, providing improved access for surgical tools and the like, when compared to previous proposals (the shorter the distance between the access area and the trailing end, the greater the access angle).

The opening may be elongate, and thus of a greater dimension in a direction along a main axis of the guide member than in a width or circumferential direction of the guide member. The opening may extend over at least half of a perimeter or circumference of the guide member. For example, the guide member may be tubular and generally circular in cross-section, and the opening may extend around half the circumference (a 180° arc) of the guide member.

The apparatus may include an inlet at a trailing end thereof for access into the apparatus. This allows one or more of a surgical tool, camera, light source, endoscope, sigmoidoscope or the like to be inserted into the apparatus and thus through the access area into the body passage.

The guide member may comprise a first end defining the leading end of the apparatus. The leading end may include an aperture, which may allow an operator to view beyond the end of the apparatus. This may also facilitate illumination of a body passage beyond the leading end.

The apparatus may comprise an expansion device moveable between collapse and expansion positions. The apparatus may be moved between collapse and expansion positions by a corresponding movement of the expansion device between the collapse and expansion positions, for expanding the body passage. The expansion device may comprise a mechanical expansion device such as an expansion arm. The expansion device is preferably flexible and elastically deformable. The expansion device may comprise a material selected from the group comprising plastics, metal or metal alloys such as a spring steel, shape memory alloys (SMAs) such as Nickel Titanium Alloy (Nitinol) or the like, or a combination thereof. The collapse position of the expansion device may comprise a rest position and the expansion position a stressed position. Alternatively, the collapse position may comprise a stressed position and the expansion position a further stressed position. In a further alternative, the collapse position may comprise a stressed position and the expansion position a rest position. For example, where the expansion device comprises a metal alloy or a SMA, the device may be curved/arcuate in the rest position, defining an expansion position for expanding the body passage. A force may be required to be exerted on the expansion device to move the device, and thus the apparatus, to a collapse position, for insertion, manipulation and removal of the apparatus from the body passage. Where the expansion device comprises a SMA, the device may be adapted to be moved to an expansion position by heating the device above a transition temperature of the metal alloy. As will be understood by those skilled in the field of SMAs, heating of an SMA above a transition temperature causes the alloy to undergo a transition to a superelastic state, thereby assuming an unstressed shape in which the device was formed.

Preferably, the expansion device is movable to the expansion position in response to an applied force, which may be controlled by the actuation device.

Alternatively, the expansion device may comprise at least one inflatable element, which may comprise a tube, ring or the like. The inflatable element may be adapted to be inflated by a pump to move the apparatus to the expansion position.

This allows fail-safe return of the apparatus to the collapse position by bleeding pressure from the inflatable element, for deflation of the elements and thus removal of the apparatus from the body passage. The expansion device may comprise two or more inflatable elements, the elements axially spaced with respect to an axis of the apparatus, for example, spaced at either axial end of the access area. The expansion device may comprise an inflatable element at or adjacent a leading end of the apparatus, and at least a second inflatable element axially spaced therefrom. On inflation, the elements may expand the body passage over part of a length of the passage defined between the elements. Where a relatively long portion of a body passage is to be expanded, more than two inflatable elements may be provided, to ensure that contraction (prolapse) of the walls of the body passage between the inflatable elements does not occur, which can restrict viewing or conduction of a procedure through the access area.

In a further alternative, the apparatus may comprise a combination of at least one elastically deformable expansion device, such as an expansion arm, and at least one inflatable element. The elastically deformable expansion device may be coupled to the inflatable element. In this fashion, expansion of the body passage is achieved through a combination of inflation of the inflatable element and deformation of the elastically deformable device. In an alternative embodiment, the expansion device may comprise at least two axially spaced inflatable elements with an elastically deformable device coupled to and extending therebetween. In a further alternative embodiment, the expansion device may comprise an inflatable element coupled to or mounted on or around an elastically deformable device such as an expansion arm. This provides a two stage expansion of the body passage. In a still further alternative, at least one elastically deformable expansion device may be provided separately from at least one inflatable element.

The apparatus may further comprise at least one light source for illuminating at least part of the body passage, which may comprise one or more light emitting diode (LED) or the like. Preferably also, the apparatus includes an image capturing device such as a video imaging camera.

The apparatus may also comprise a cover for preventing damage to the body passage due to insertion, removal, expansion or collapse of the apparatus. The cover may comprise a membrane and may be coupled to or form part of the expansion device, preferably, the/each expansion arm.

The apparatus may be disposable and may be of a plastics material.

According to a second aspect of the present invention, there is provided medical apparatus adapted for location at least partly within a body passage, the apparatus comprising a leading end defining an opening for access from the apparatus into the body passage and at least one inflatable element adapted for inflation to controllably move the apparatus between collapse and expansion positions, for expanding the body passage.

Preferably, an inflatable element is located at or adjacent the leading end, for expanding the body passage at a location near the opening, to facilitate access to the body passage.

According to a third aspect of the present invention, there is provided a method of providing access to a body passage, the method comprising the steps of:

inserting a medical apparatus at least partly into a body passage with the apparatus in a collapse position;

controllably moving the apparatus from the collapse position to an expansion position, to expand the body passage; and accessing the body passage through an access area of the apparatus, at least part of the access area being spaced from a leading end of the apparatus.

According to a fourth aspect of the present invention, there is provided a method of inspecting a body passage, the method comprising the steps of:

inserting a medical apparatus at least partly into a body passage with the apparatus in a collapse position;

controllably moving the apparatus from the collapse position to an expansion position, to expand the body passage; and viewing the body passage through an access area of the apparatus, at least part of the access area being spaced from a leading end of the apparatus.

According to a fifth aspect of the present invention, there is provided a method of conducting surgery within a body passage, the method comprising the steps of:

inserting a medical apparatus at least partly into a body passage with the apparatus in a collapse position;

controllably moving the apparatus from the collapse position to an expansion position, to expand the body passage; and inserting at least one surgical tool into the body passage through an access area of the apparatus, at least part of the access area being spaced from a leading end of the apparatus.

The method may comprise exerting an expansion force on the medical apparatus following insertion into the body passage, to move the apparatus to the expansion position. Alternatively, the method may comprise exerting a collapse force on the medical apparatus, to restrain the apparatus in a collapse position for insertion into the body passage, and subsequently releasing or removing the collapse force, to allow the medical apparatus to move to the expansion position.

The method may further comprise controllably moving the apparatus from the expansion position to the collapse position and removing the apparatus from the body passage. The medical apparatus may then be rotated relative to the body passage, reinserted into the body passage and again moved to the expansion position. It will be understood that this allows a progressive inspection of a circumference of part of an internal wall of the body passage. The method may alternatively comprise returning the apparatus to the collapse position and rotating the medical apparatus within the body passage, and then again controllably moving the apparatus to the expansion position.

The method of inspecting the body passage may comprise providing imaging apparatus such as a video imaging camera for viewing the body passage through the access area. The method of inspecting the body passage may further comprise conducting a diagnostic procedure, for example, taking a sample of material, such as part of a tumour/lesion on the body passage.

BRIEF DESCRIPTION OF THE DRAWINGS

Embodiments of the present invention will now be described, by way of example only, with reference to the accompanying drawings, in which:

FIGS. 65-68 are perspective, side, plan and end views of a medical apparatus in accordance with a yet further alternative embodiment of the present invention, shown in an expansion position;

FIGS. 82 and 83 are perspective and side views, respectively, of an expansion device forming part of a further alternative medical apparatus; and FIG. 84 is a perspective view of an expansion device forming part of a further alternative medical apparatus.

DETAILED DESCRIPTION OF THE PREFERRED EMBODIMENTS

Figure 1:
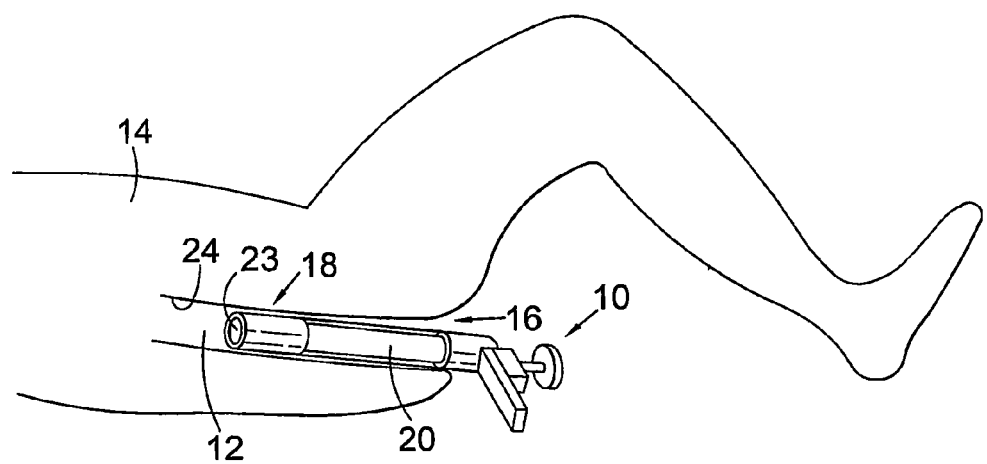
FIG. 1 is a schematic view of medical apparatus in accordance with a preferred embodiment of the present invention, the medical apparatus shown in use and in a collapse position.

Turning firstly to FIG. 1, there is shown a schematic view of medical apparatus in accordance with a preferred embodiment of the present invention, the medical apparatus shown in use and indicated generally by reference numeral 10. The medical apparatus takes the form of a rectal expander having a particular utility in transanal endoscopic microsurgery (TEM), and is shown in use during a TEM procedure.

The rectal expander 10 is adapted for location at least partly within a body passage, and is shown in FIG. 1 located in a rectum 12 of a patient 14, the expander 10 inserted into the rectum 12 via the patient's anus 16. The expander 10 has a leading end 18 and an access area in the form of an opening 20 for access from the expander 10 into the rectum 12, and at least part of the opening 20 is spaced from the expander leading end 18. The expander 10 is controllably moveable between rest, collapse and stressed expansion positions for expanding the rectum 12, and is shown in FIG. 1 in the collapse position. The expander 10 is inserted into the rectum 12 in the collapse position, and is then controllably moved to an expansion position, illustrated schematically in FIG. 2, to expand a portion 21 of the rectum 12.

As will be described in more detail below, expansion of the rectum 12 in this fashion facilitates access into and inspection of the rectum, as well as any diagonostic or surgical procedure to be conducted within the rectum 12. This is because the expander 10 provides improved access when compared to prior proposals. As noted above, the rectal expander 10 has a particular utility in TEM procedures, such as in the location and inspection of tumours/lesions in the rectum 12, and in subsequent removal and/or treatment.

Turning now to FIGS. 3-6, there are shown rear perspective, top perspective, side and hidden detail side views, respectively, of the rectal expander 10 in the collapse position of FIG. 1. The expander 10 includes an expansion device comprising two elastically deformable expansion arms 22, which are controllably moveable between collapse and expansion configurations for elastically expanding a wall 24 of the rectum 12.

Figure 2:
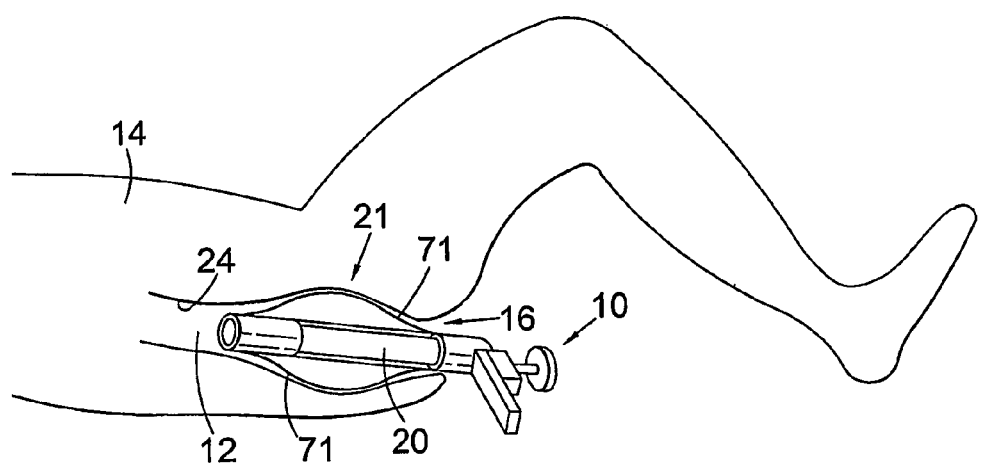
FIG. 2 is a view of the apparatus of FIG. 1 in an expansion position.
Figure 3:
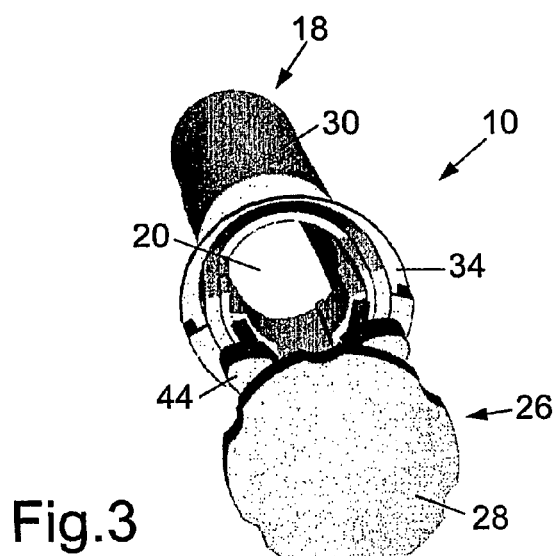
FIGS. 3-6 are enlarged, detailed rear perspective, top perspective, side and hidden detail side views of the apparatus of FIG. 1 in the collapse position.
Figure 4:
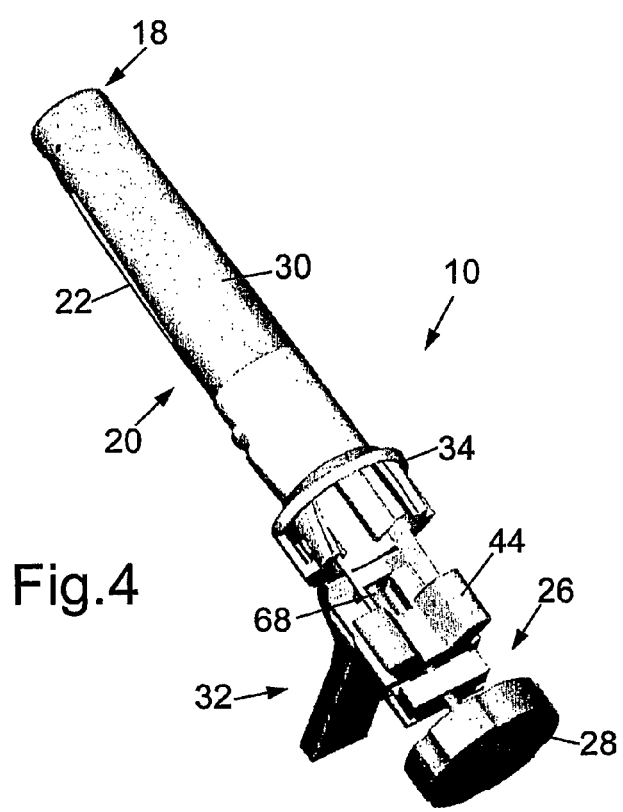
Figure 5:
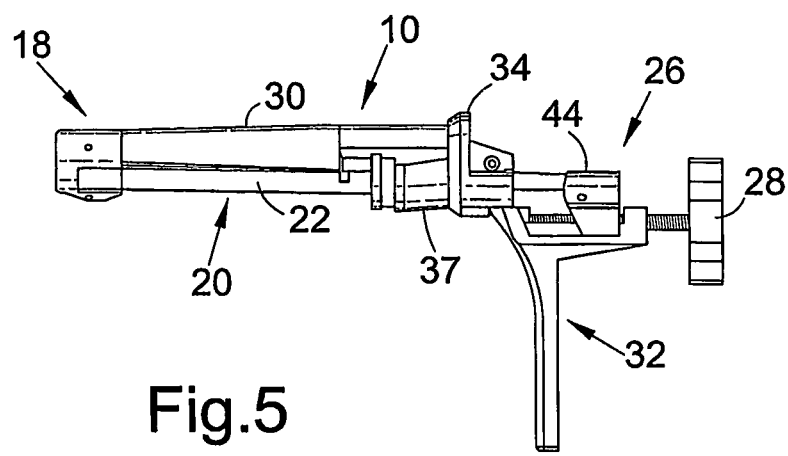
Figure 6:
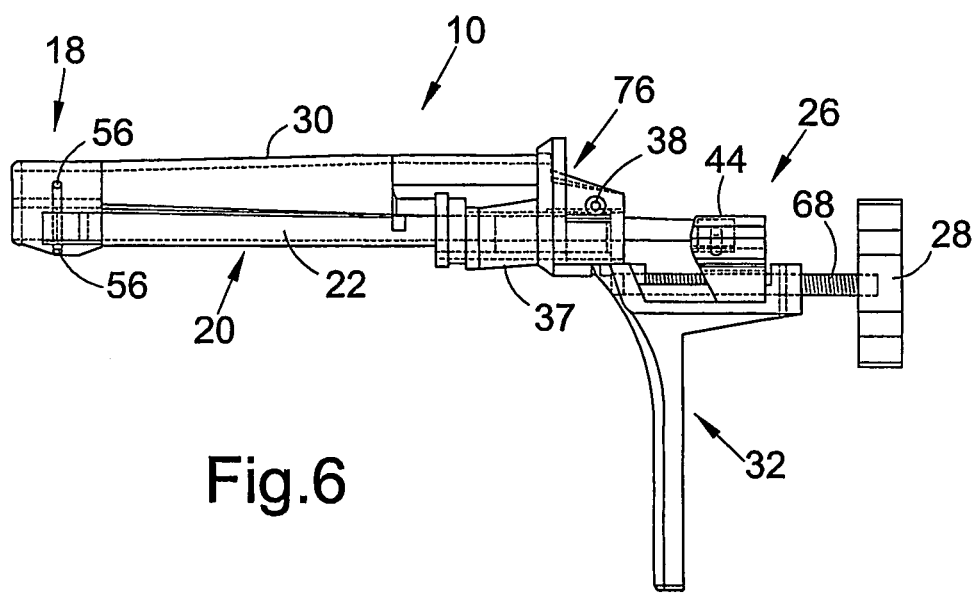
Figure 7:
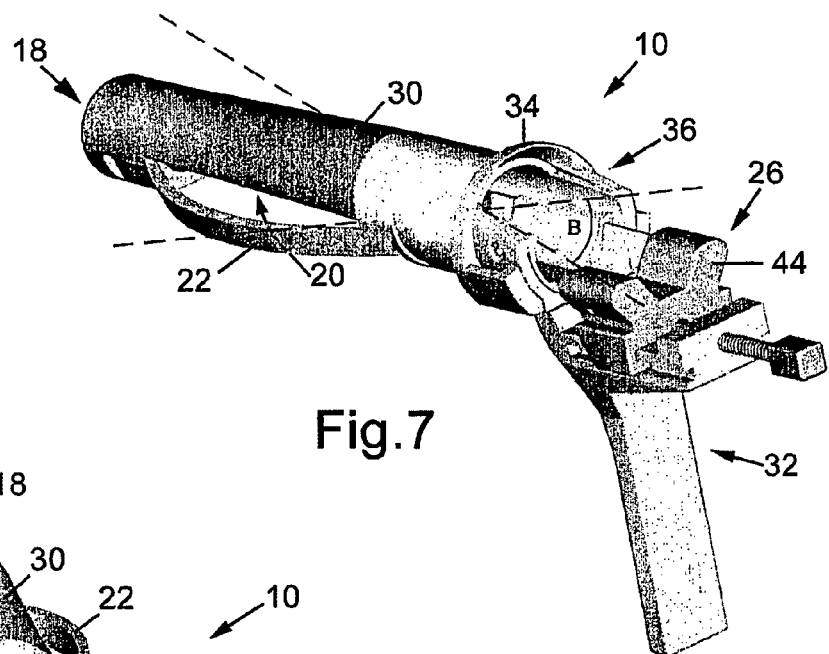
FIGS. 7 and 8 are enlarged, detailed top and rear perspective views of the apparatus of FIG. 1 in the expansion position.
Figure 8:
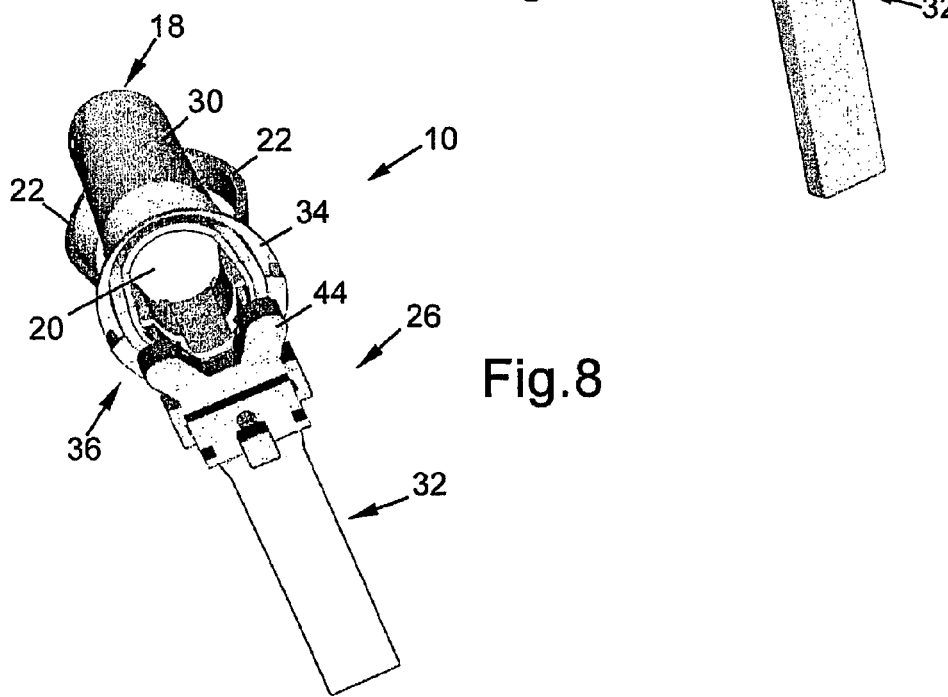
Figure 9:
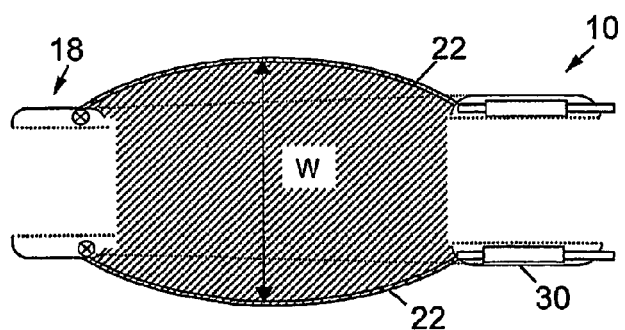
FIG. 9 is a longitudinal half-sectional view of the apparatus of FIG. 1 in the expansion position.

The arms 22 are shown more clearly in FIGS. 7 and 8, which are views of the expander 10 following movement of the arms 22 to the expansion position, corresponding to the expansion position of the expander shown in FIG. 2. The arms 22 are also shown in FIG. 9 which is a longitudinal half sectional view of part of the rectal expander 10 in the expansion position, viewed from above. FIG. 9 illustrates the potential maximum width W of the opening 20, which has been shaded to illustrate the potential access using the expander 10.

Figure 11:
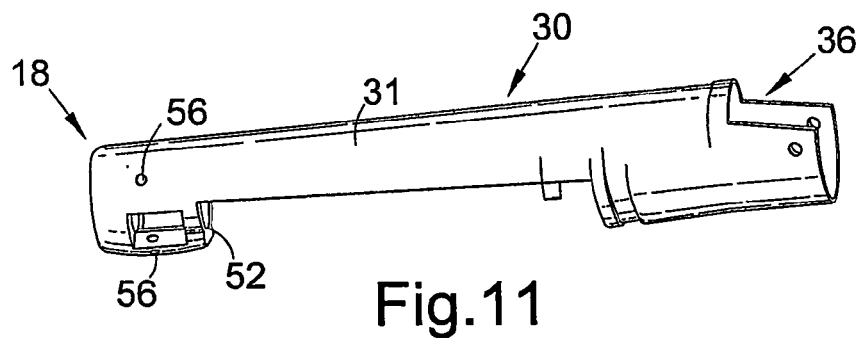
Figure 12:
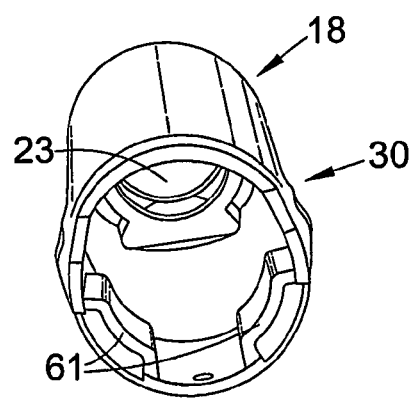
Figure 13:
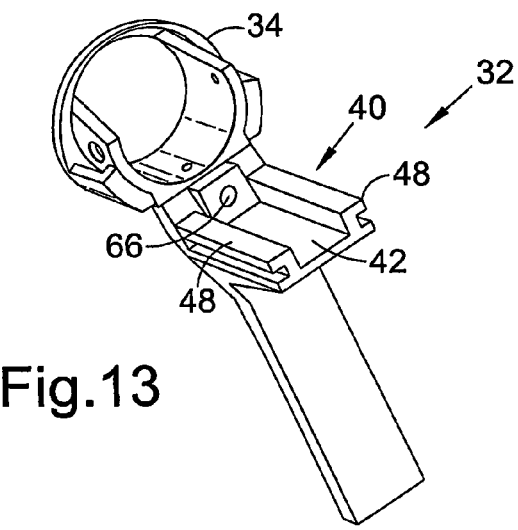
FIGS. 13-16 are enlarged, detailed perspective, side, plan and end views, respectively, of a handle forming part of the apparatus of FIG. 1.
Figure 14:
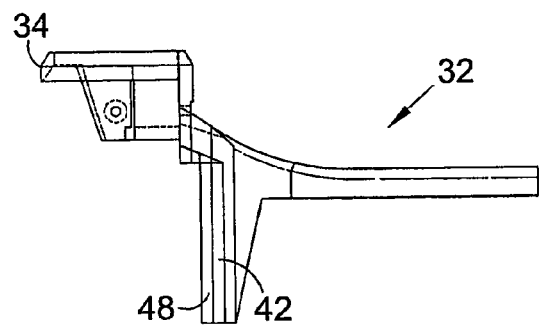
Figure 15:
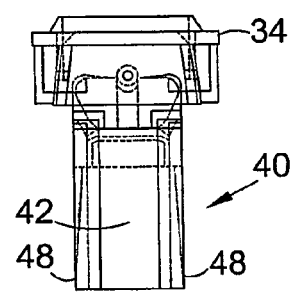
Figure 16:
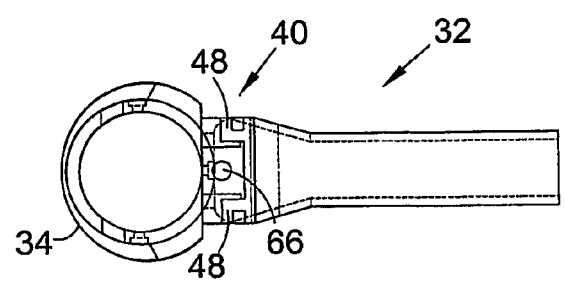
Figure 17:
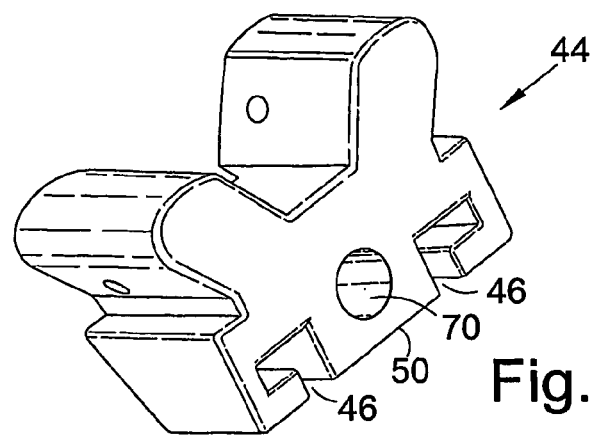
FIGS. 17-20 are enlarged, detailed perspective, side, plan and end views, respectively, of an activation member forming part of the apparatus of FIG. 1.
Figures 18, 19:
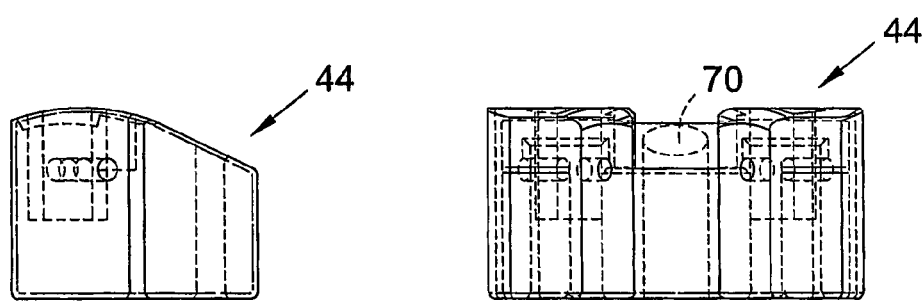
Figure 20:
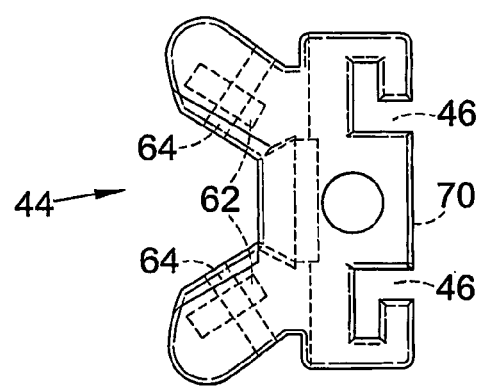

The expander 10 includes an actuating device and lock in the form of a screw mechanism 26, which mechanically moves the expansion arms 22 between the collapse and expansion positions, by rotation of an activating wheel 28. The expander 10 also includes a guide member in the form of a hollow extension tube 30, shown in more detail in the side, perspective and end views of FIGS. 10, 11 and 12. The tube 30 includes a generally semi-circular portion 31 defining the opening 20, and also defines the leading end 18 of the expander. It will be noted that the opening 20 is spaced from the leading end 18 of the tube, for reasons which will be discussed in more detail below.

The guide tube 30 is coupled to a handle 32, shown in the perspective, side, plan and end views of FIGS. 13, 14, 15 and 16, respectively. The handle 32 includes a mounting ring 34 which is mounted around a trailing end 36 of the guide tube 30 and secured to the guide tube by mounting screws or pins 38. The handle 32 also includes an extension 40 defining a track 42 on which an activating member of the actuating device, in the form of a slider 44, is mounted. The slider 44 is shown in more detail in the perspective, side, plan and end views of FIGS. 17, 18, 19 and 20, respectively. The slider 44 includes grooves 46 which slideably engage tongues 48 of the extension 40, whilst a central portion 50 of the slider 44 is mounted in sliding engagement with the track 42.

Figure 10:
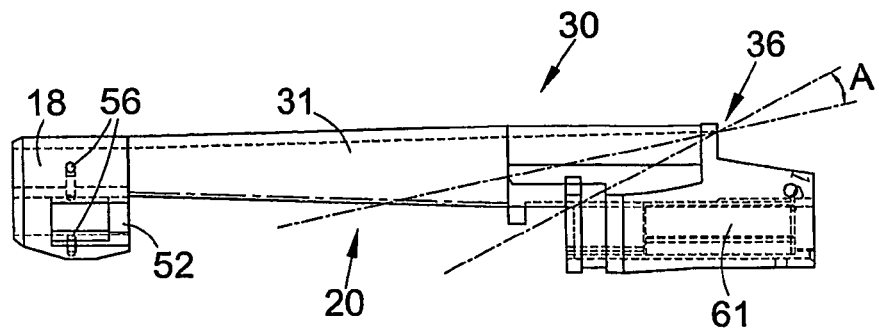
FIGS. 10, 11 and 12 are enlarged, detailed side, perspective and end views of a guide tube forming part of the apparatus of FIG. 1.
Figure 21:
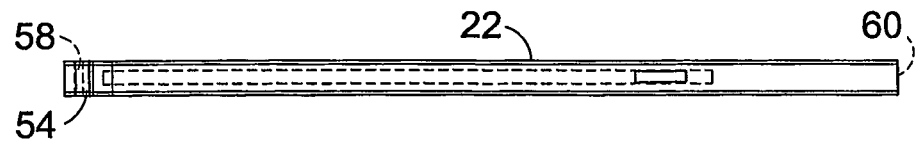
FIGS. 21 and 22 are enlarged, detailed side and plan views of an expansion device forming part of the apparatus of FIG. 1.
Figure 22:
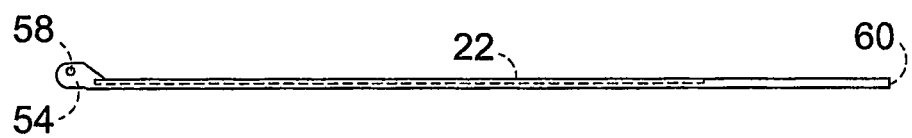

The expansion arms 22, which are shown in more detail in the side and plan views of FIGS. 21 and 22, are mounted between the leading end 18 of the guide tube 30 and the slider 44. The arms 22 are elastically deformable and typically of a plastics material, a metal or metal alloy such as spring steel, or a shape memory alloy (SMA) such as Nitinol, or a combination thereof. As shown in FIG. 10, the guide tube 30 includes recesses 52 in the generally circular leading end 18 which receive the leading ends 54 of the expansion arms 22. The expansion arms 22 are pivotally coupled to the leading end 18 by a pivot pin (not shown), which is mounted in passages 56 in the leading end and engages a pivot hole 58 in front ends 54 of the expansion arms. Rear ends 60 of the expansion arms 22 pass through guides 61 (FIG. 12) within the trailing end 36 of the guide tube 30, and are engaged in slots 62 in the slider 44 and retained by screws or pins 64. The expansion arms 22 are thus pivotally mounted to the leading end 18 of the guide tube 30 whilst the rear ends 60 of the expansion arms are mounted to the slider 44, for axial movement with respect to the guide tube 30.

The handle 32 also includes a screw passage 66 which receives an unthreaded end of a screw 68 of the screw mechanism 26. The screw 68 extends through a corresponding threaded screw hole 70 in the slider 44, and the activating wheel 28 is mounted at the free end of the screw 68. Rotation of the activating wheel 28 thus causes a corresponding rotation of the screw 68, translating the slider 44 along the extension 40. This is facilitated by sliding engagement between slider central portion 50 and track 42, and between the tongues 48 and slider grooves 46. This movement shortens the distance between the front and rear ends 54, 60 of the expansion arms 22, stressing the arms and urging them towards the expansion position of FIG. 2 and FIGS. 7-9, where they adopt a curved or arcuate shape.

This movement continues until the rectum 12 has been expanded to a desired degree. Movement of the expansion arms is ultimately stopped when the slider 44 comes into contact with the handle mounting ring 40. Following movement of the expander 10 to the desired expansion position, the activating wheel 28 can be removed, as shown in FIGS. 7 and 8, to facilitate access to the rectum 12.

Figure 23:
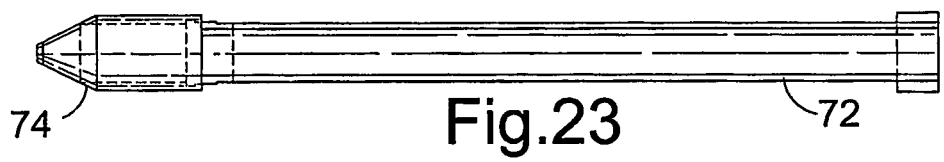
FIG. 23 is a view of an insertion device for the apparatus of FIG. 1.
Figure 24:
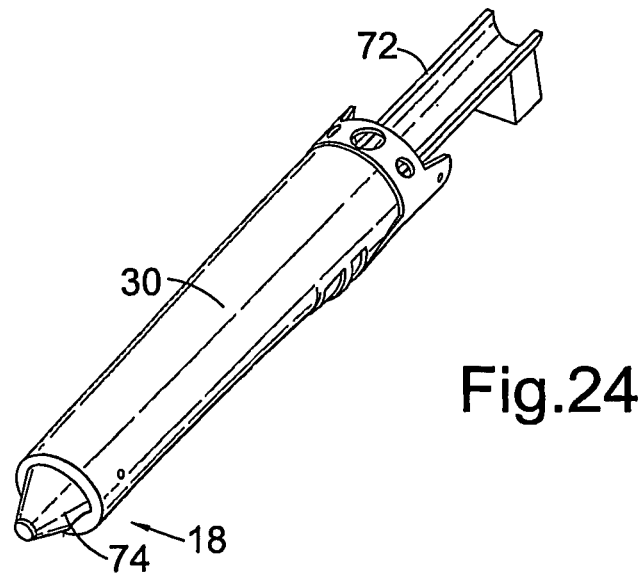
FIG. 24 is a view showing insertion of the guide tube of FIGS. 10 to 12 during insertion using the insertion device of FIG. 23.
Figure 25:
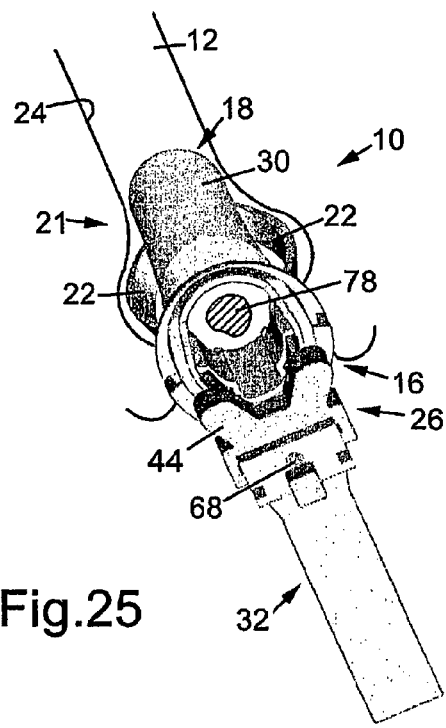
FIGS. 25 and 26 are schematic views of steps in a surgical procedure using the apparatus of FIG. 1.

The method of operation of the rectal expander 10 will now be described in more detail with reference also to FIG. 23, which is a view of an insertion device in the form of an obturator 72 for inserting the guide tube 30, and FIG. 24, which is a perspective view of the obturator 72 engaged within the guide tube 30. FIG. 25 shows obturator 72 engaging with tube 30, arm 22, mechanism 26 and handle 32.

The rectal expander 10 allows access to a body passage, such as the rectum 12 of the patient 14, for inspection purposes as well as for conducting surgery. The expander 10 may have a particular use in TEM such as for locating and performing surgery on a tumour in the rectum 12. The expander 10 is inserted into the rectum 12 through the anus 16 in the collapse position of FIGS. 1, 3 and 4, optionally using the obturator 72, which is mounted within the guide tube 30 with an end 74 engaging the leading end 18 of the guide tube, as shown in FIG. 24. The obturator 72 is then removed. Alternatively, it will be understood that the expander 10 may be inserted without the aid of the obturator 72.

The activating wheel 28 is then attached and rotated to advance the slider 44 along the extension 40 towards the guide tube 30, stressing the expansion arms 22 and moving them out to the expansion position of FIGS. 2 and 7-9. Membranes 71 (FIG. 2) prevent prolapse of the rectum wall 24 into the space between the expansion arms 22 and the guide member 30.

A surgeon may then view the expanded rectum wall 24 through the aperture 20 in the guide tube 30, to determine whether a tumour or other irregularity is present. This is achieved using an endoscope, sigmoidoscope or a video imaging camera (not shown). A light source such as one or more light emitting diodes (LEDs) may also be provided for illuminating the rectum 12. Elastic expansion of the rectum wall 24 opens out the wall, thereby facilitating location of a tumour or other irregularity which cannot otherwise be viewed or accessed. Inspection of the rectum 12 around a 360° arc is achieved by returning the expander 10 to the collapse position, rotating the expander relative to the rectum 12, and returning the expander to the expansion position of FIG. 2, and then repeating this process as required. The expander may be rotated internally or externally of the rectum 12.

Figure 26:
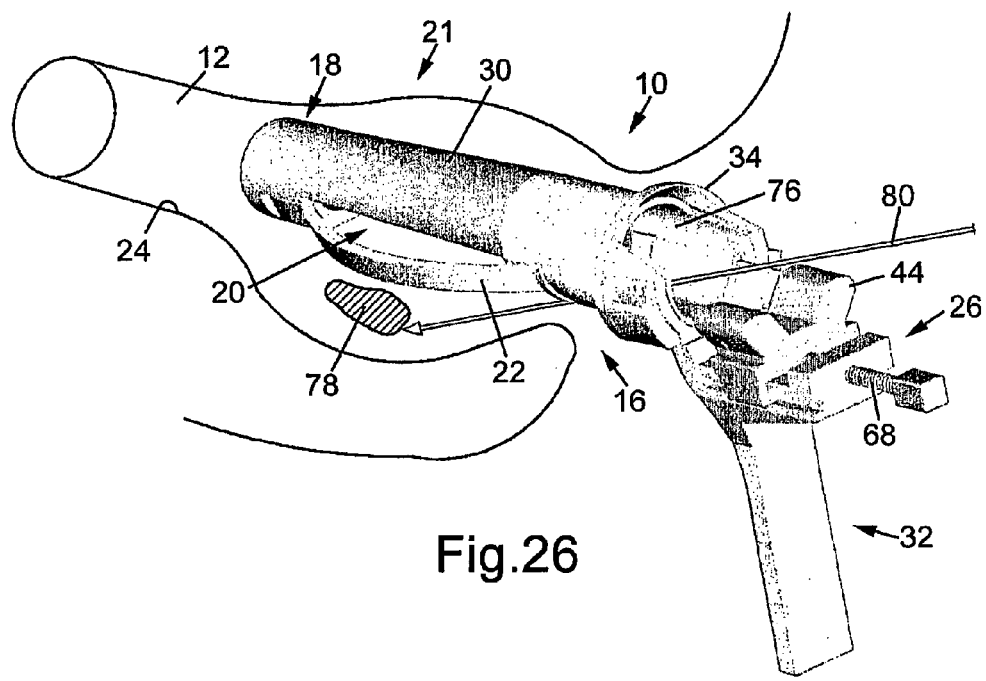

On detection of a tumour or other irregularity, the expander 10 then allows a surgical procedure to be conducted, such as a TEM procedure. This is achieved by inserting surgical tools through an inlet 76 defined by the trailing end 36 of the guide tube 30 and a handle mounting ring 34, as illustrated in the schematic views of FIGS. 25 and 26. The tube trailing end 36 is angled to facilitate insertion and manipulation of the surgical tools. In FIG. 25, a tumour 78 is shown adjacent the expander opening 20 viewed by a surgeon using an endoscope or the like, as discussed above. In FIG. 26, part of a diagnostic/surgical procedure for treating the tumour 78 is illustrated, where a cutting or cauterising tool 80 has been inserted through the inlet 76, along guide tube 30 and through opening 20. Access and viewing through an aperture 23 in the tube leading end 18 is also possible. It will be understood that the dimensions and location of the opening 20, and the short axial length of the circular portion 37 of the guide tube 30 allow the surgeon to manipulate the cutting tool 80 in a fashion not possible with prior proposals. This is because the expander 10 allows manipulation of surgical tools over a wide angle A in the vertical plane (FIG. 10) and B in the horizontal plane (FIG. 7). This improves the ability to locate, view, access and thus treat abnormalities such as the tumour 78.

It will also be understood that the screw mechanism 26 allows controllable movement of the apparatus from the collapse position of FIG. 1 to the expansion position of FIG. 2. This is because the surgeon may choose to locate the expander 10 in a position intermediate the collapse and expansion positions, if he determines that this is appropriate or required in a particular case. The screw mechanism 26 is also self-locking in the set position by friction between the moving parts of the mechanism. The expander 10 also provides the surgeon with a feedback of the force exerted on the rectum 12 during expansion. This is because the surgeon can sense the force applied to the rectum wall 24 during expansion, as the relative resistance to rotation of the activating wheel 28 increases as the rectum becomes increasingly expanded.

Turning now to FIGS. 27-30, there is shown a rectal expander 110 in accordance with an alternative embodiment of the present invention. Like components of the rectal expander 110 with the expander 10 of FIGS. 1-26 share the same reference numerals, incremented by 100. Only the substantial differences between the expander 110 and the expander 10 will be described herein in detail.

Figure 27:
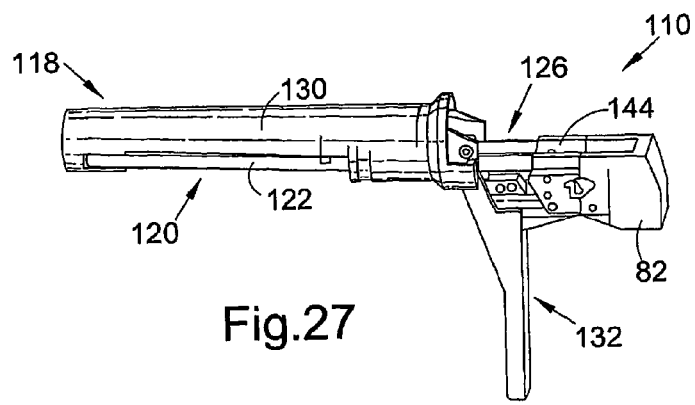
FIGS. 27 and 28 are side and hidden detail side views of medical apparatus in accordance with an alternative embodiment of the present invention, shown in a collapse position.
Figure 28:
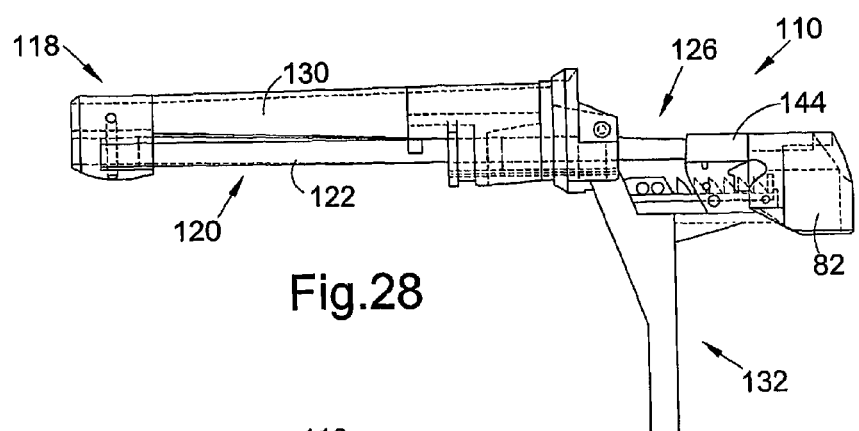
Figure 29:
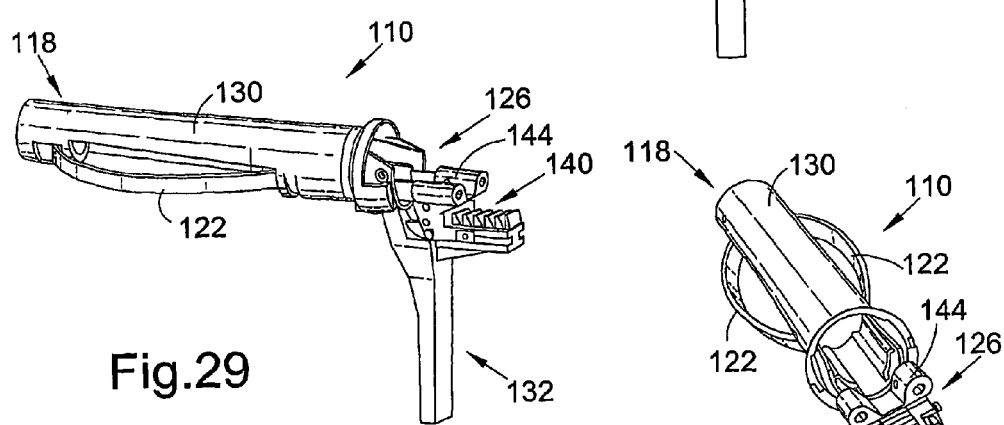
FIGS. 29 and 30 are side and top perspective views of the apparatus of FIG. 27 in an expansion position.
Figure 30:
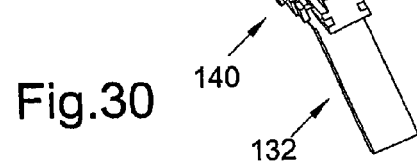
Figure 31:
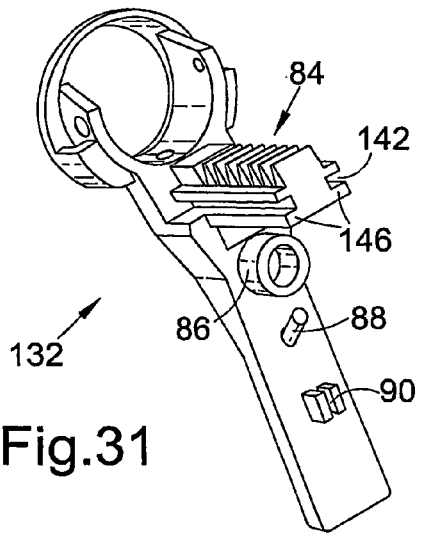
FIGS. 31-34 are perspective, side, plan and end views of a handle forming part of the apparatus of FIG. 27.
Figure 32:
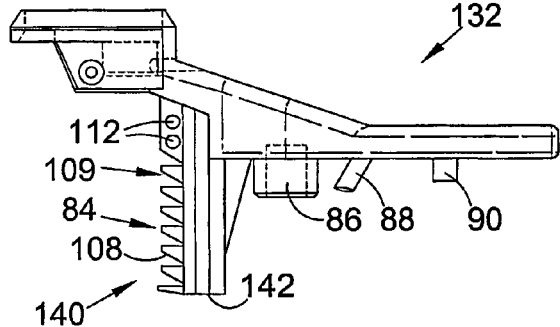
Figure 33:
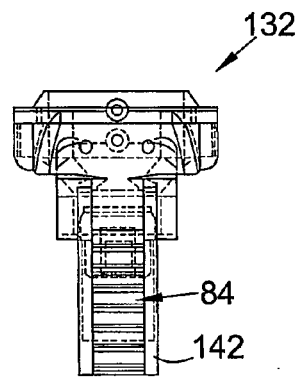
Figure 34:
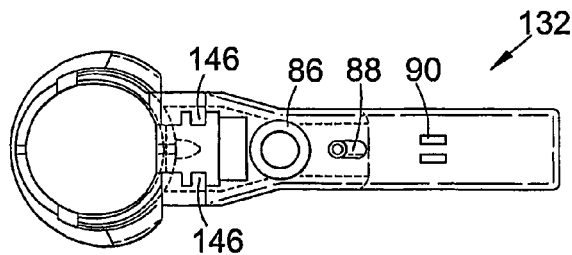
Figure 35:
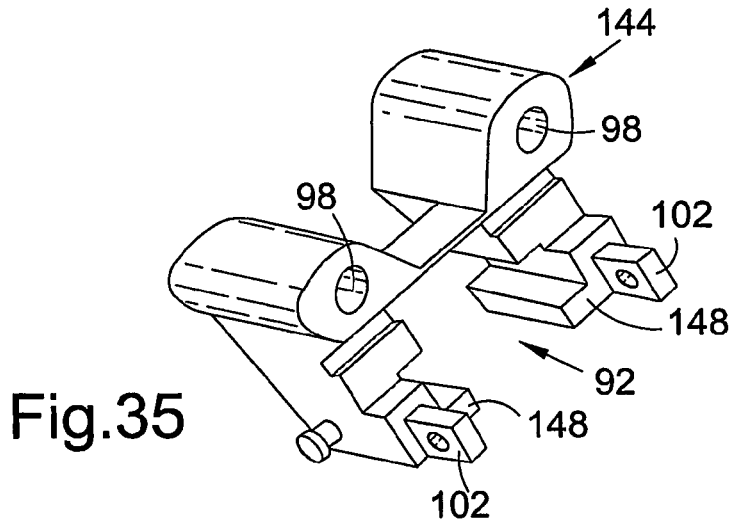
FIGS. 35-38 are perspective, side, plan and end views of an activating member forming part of the apparatus of FIG. 26.
Figure 36:
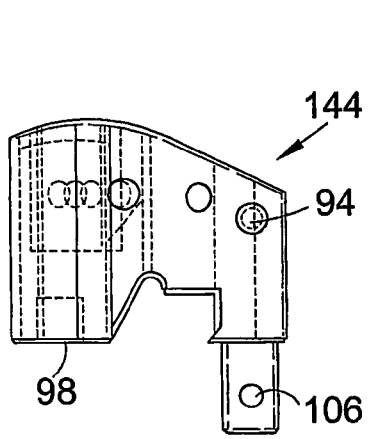
Figure 37:
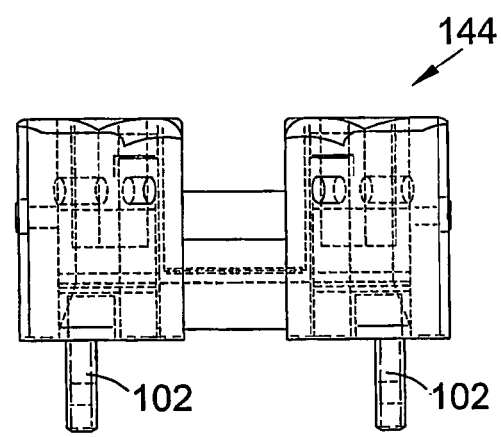
Figure 38:
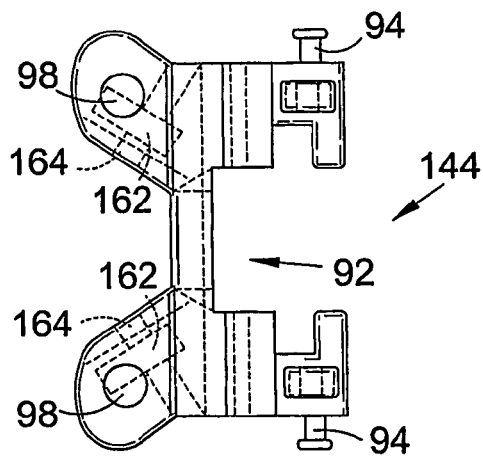
Figure 39:
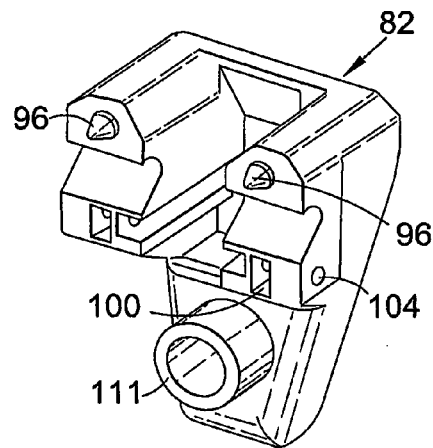
FIGS. 39-42 are perspective, side, plan and end views of a locking handle forming part of the apparatus of FIG. 27.
Figure 40:
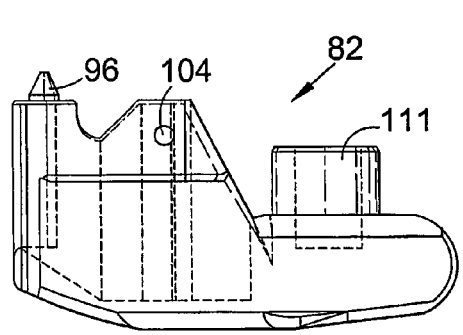
Figure 41:
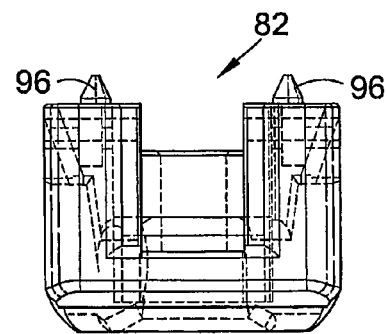
Figure 42:
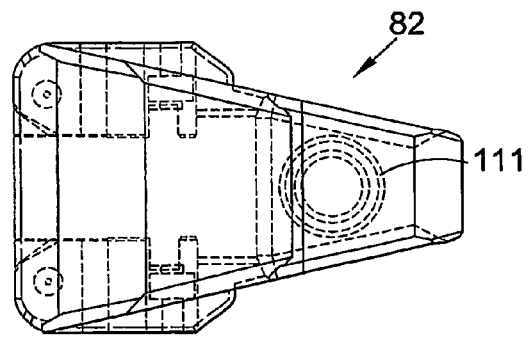

The expander 110 is shown in FIGS. 27 and 28 in a collapse position and in FIGS. 29 and 30 in an expansion position. The expander 110 includes a handle 132 but with an alternative actuating device and lock comprising a ratchet mechanism 126 and a locking handle 82.

The handle 132 is shown in more detail in the enlarged perspective, side, plan and end views of FIGS. 31, 32, 33 and 34, respectively. The handle 132 includes an extension 140 having a track 142 carrying ratchet teeth 84. The handle 132 is also illustrated in FIGS. 31-34 including an optional boss 86 for engaging a return spring (not shown), and a stub 88 and rod engaging teeth 90. The stub 88 and teeth 90 provide a mounting for a clip (FIG. 43) which extends through slider 144 and locks in holes 112 in the handle 132, to clamp the expansion arms 122 in the expansion position for long term operation. This is optional and in addition to pawl 85 which engages the ratchet teeth 84.

The slider 144, shown in the perspective, side, plan and end views of FIGS. 35, 36, 37 and 38, respectively, defines a channel 92 for mounting the slider 144 on the track 142, and tongues 148 which slidably engage in grooves 146 in the handle extension 140. A spring biased pawl 85 (FIG. 43/45) is mounted between stubs 94 and biased into engagement with ratchet teeth 84 when the slider 144 is mounted on the extension 140. The angle of the ratchet teeth 84 is such that the slider 144 may be advanced along the track 142 towards the guide tube 130 but is prevented from return movement by the pawl 85, until the pawl is manually lifted free from the ratchet teeth by the surgeon.

The locking handle 82 is shown in more detail in the enlarged perspective, side, plan and end views of FIGS. 39, 40, 41 and 42 and includes locating pins 96 which engage recesses 98 in the slider 144. The locking handle 82 also includes slots 100 which engage bars 102 on the slider 144 and which are locked by pins (not shown) engaging pin holes 104 and 106 in the handle 82 and slider 144, respectively. An optional boss 111 on the locking handle 82 allows for mounting of the return spring between the boss 111 and the handle boss 86.

The rectal expander 110 is used in a similar fashion to the expander 10 of FIGS. 1-26. Movement to the expansion position is achieved by manually exerting a force on the slider 144 through the handle 82, which advances the slider along the track 142. During this movement, the sprung pawl 85 is lifted or travels up angled faces 108 of the ratchet teeth 84, engaging in troughs 109 to restrain movement of the slider. When the expander 110 has been moved to the expansion position, the handle 82 can be removed, as shown in FIGS. 29 and 30, for access through the opening 120.

Figure 43:
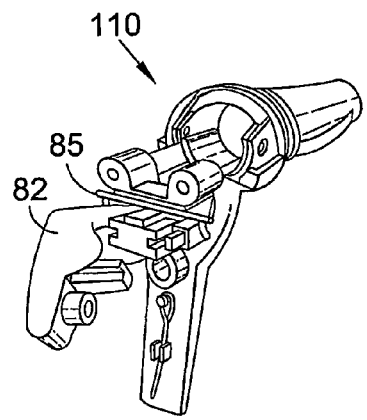
FIGS. 43 & 44 are views of the apparatus of FIG. 27 showing a locking member of the apparatus, with a locking handle removed, and with the locking handle engaged, respectively.
Figure 44:
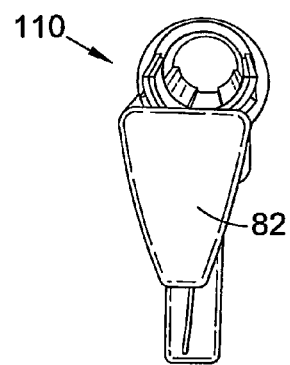
Figure 45:
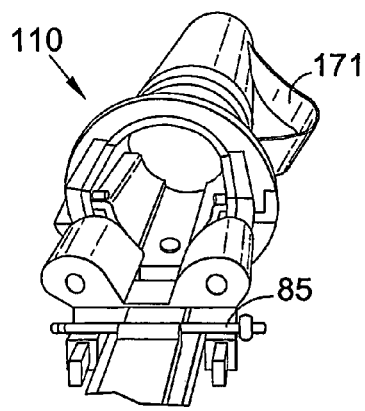
FIGS. 45 and 46 are views of the apparatus of FIG. 27 in the expansion position illustrating membranes of the expander.
Figure 46:
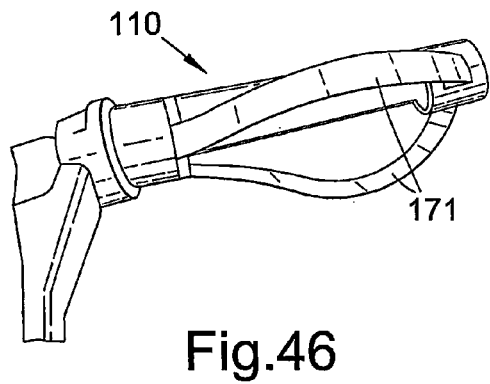

FIG. 43 is a view of the expander 110 in the collapse position showing the sprung pawl 85 and with the locking handle 82 removed. FIG. 44 shows the locking handle 82 engaged to the slider 144. FIGS. 45 and 46 are views showing the expander 110 in the expansion position and illustrate the membranes 171.

Figure 47:
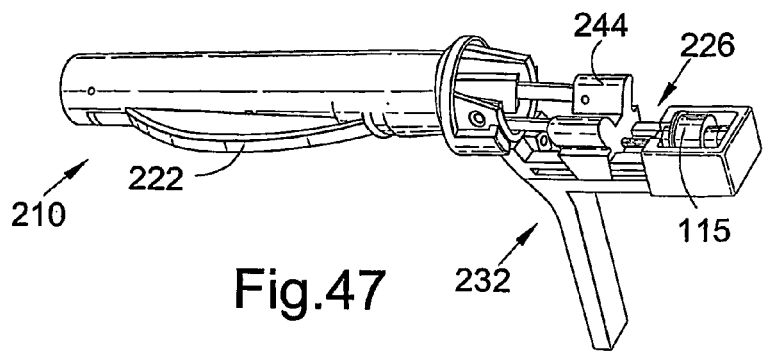
FIG. 47 is a perspective view of medical apparatus in accordance with a further alternative embodiment of the present invention, shown in an expansion position.
Figure 48:
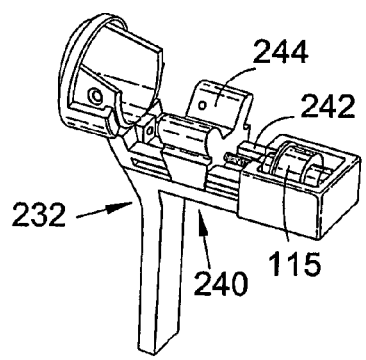
FIGS. 48-51 are perspective, side, plan and end views of part of the apparatus of FIG. 47.
Figure 49:
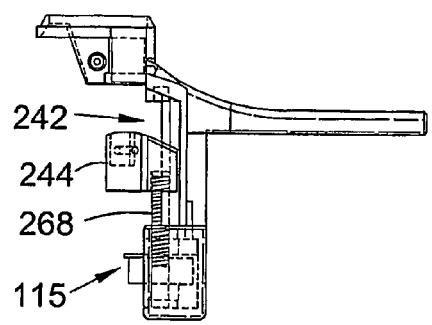
Figure 50:
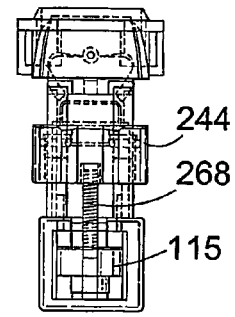
Figure 51:
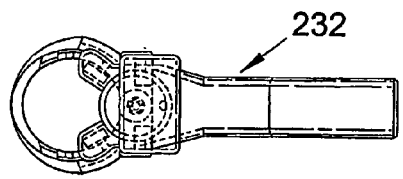

Turning now to FIG. 47, there is shown a rectal expander 210 in accordance with an alternative embodiment of the present invention. Like components of the expander 210 with the expander 10 of FIGS. 1-26 share the same reference numerals incremented by 200. For brevity, only the differences between the expander 210 and the expander 10 will be described in detail.

A handle 232 of the expander 210 is shown in more detail in the perspective, side, plan and end views, respectively of FIGS. 48, 49, 50 and 51. The expander 210 includes an activation and locking device in the form of a driven screw mechanism 226. The driven screw mechanism 226 includes an electrically activated linear actuator 115 (motor) which rotates a screw 268 coupled to slider 244, for advancing and retracting the slider 244 in a controllable fashion along track 242 of the handle extension 240. This allows precise control of movement of the expansion arms 222 between a collapse position and an expansion position shown in FIG. 47.

Figure 52:
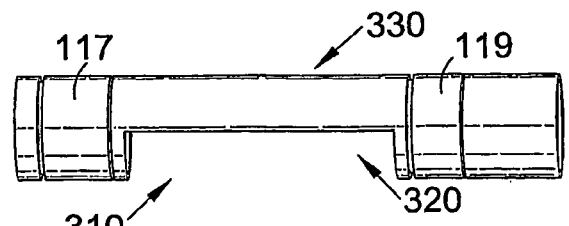
FIG. 52 is a side view of part of a medical apparatus in accordance with a still further alternative embodiment of the present invention, shown in a collapse position.

Turning now to FIG. 52, there is shown part of a rectal expander 310 in accordance with a further alternative embodiment of the present invention. Like components of the expander 310 with the expander 10 of FIGS. 1-26 share the same reference numerals, incremented by 300.

The expander 310 includes a guide tube 330 and first and second inflatable elements 117, 119. The expander 310 is shown in FIG. 52 in the collapse position, where the elements 117, 119 are deflated.

Figure 53:
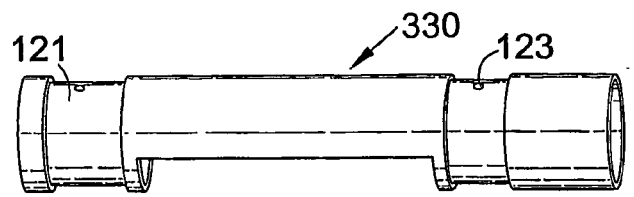
FIGS. 53 and 54 are perspective and side views of a guide member forming part of the apparatus of FIG. 52.
Figure 54:
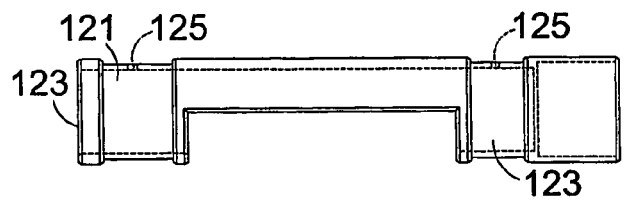

FIGS. 53 and 54 are perspective and side views, respectively, of the guide tube 330 with the inflatable elements 117, 119 removed. It will be noted that the tube 330 includes recesses 121, 123 which receive the elements 117, 119. This ensures that the elements 117, 119 do not protrude from the guide tube 330, facilitating insertion and retraction. The guide tube 330 includes air holes 125 for inflating the elements 117, 119 through a pump (not shown) coupled to the elements through supply tubes. There is an approximately proportional relationship between pressure of air in the elements 117, 119 and the corresponding expansion diameter of the elements.

Figure 55:
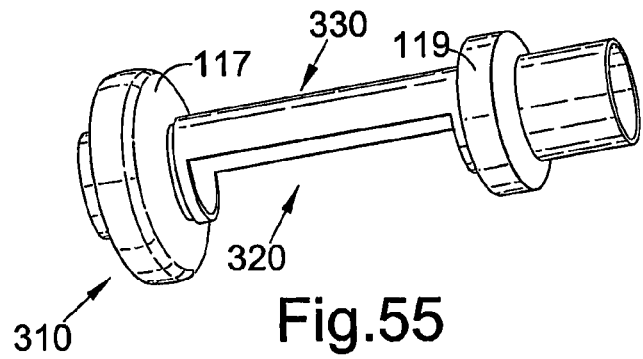
FIGS. 55 and 56 are perspective and side views of the apparatus of FIG. 52, shown in an expansion position.
Figure 56:
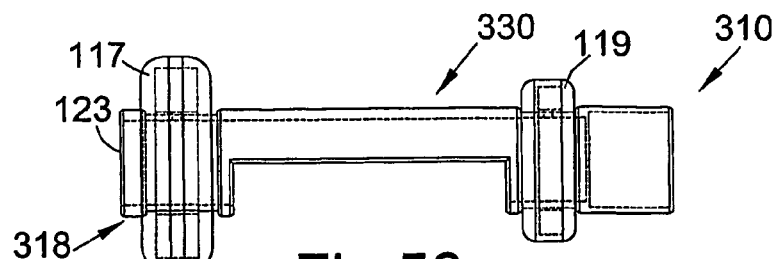
Figure 57:
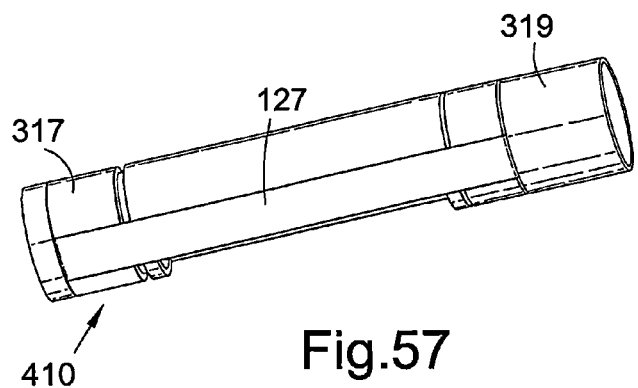
FIGS. 57-60 are perspective, side, plan and end views of a medical apparatus in accordance with a still further alternative embodiment of the present invention, shown in a collapse position.
Figure 58:
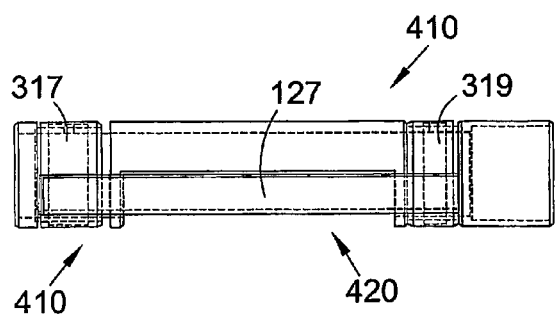
Figure 60:
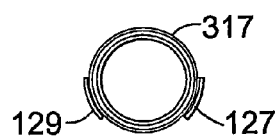
Figure 59:
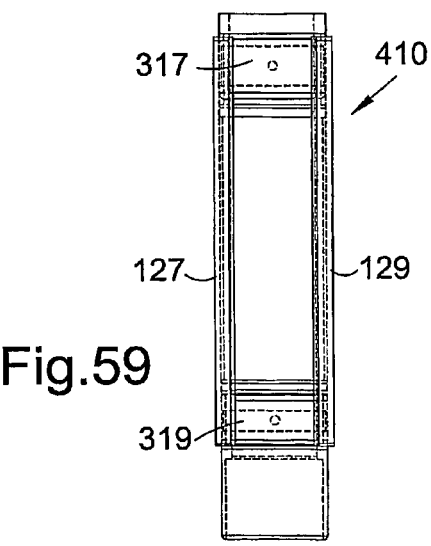
Figure 61:
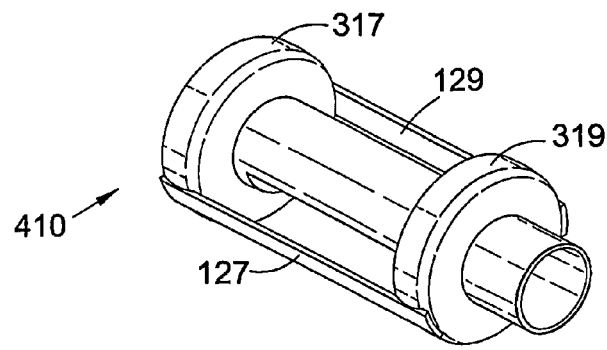
FIGS. 61-64 are perspective, side, plan and end views of the apparatus of FIG. 57 shown in an expansion position.
Figure 62:
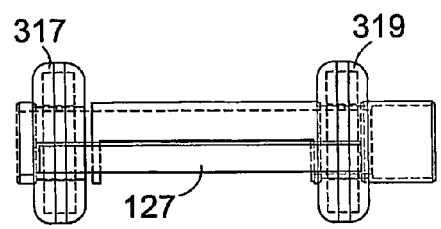
Figure 63:
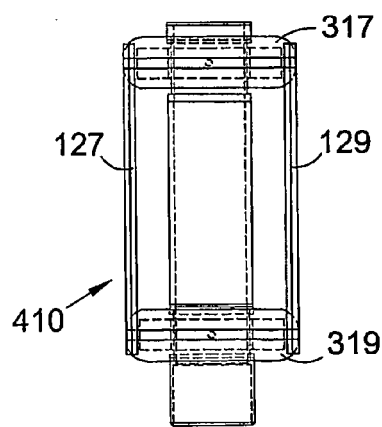
Figure 64:
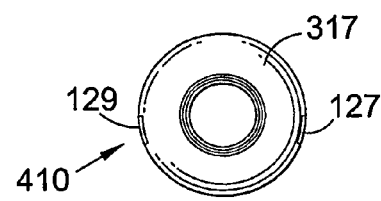
Figure 69:
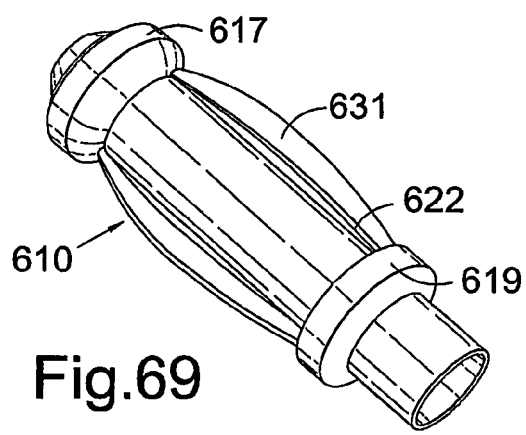
FIGS. 69-72 are perspective, side, plan and end views of a medical apparatus in the form of a rectal expander in accordance with a yet further alternative embodiment of the present invention, shown in an expansion position.
Figure 70:
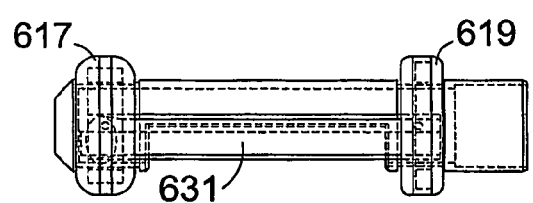
Figure 71:
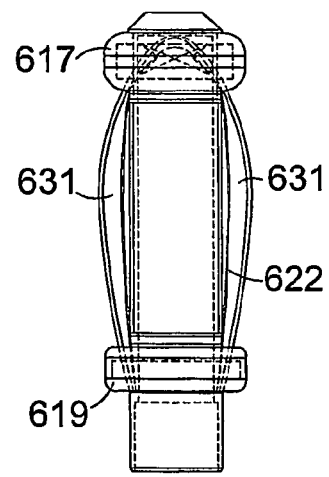
Figure 72:
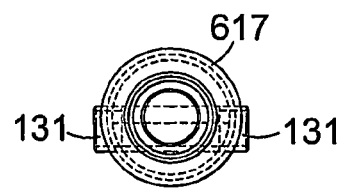

The expander 310 is shown in the perspective and side views of FIGS. 55 and 56 following inflation of the elements 117, 119, where the expander 310 is in an expansion position. It will be noted that the element 117, which is located adjacent a leading end 318 of the guide tube 330, expands to a larger external diameter than the element 119.

This causes a greater expansion of the rectum 12 adjacent the leading end 318, facilitating access and viewing of the rectum 12 beyond the leading end 318 through an aperture 123 in the leading end 318.

Turning now to FIGS. 57, 58, 59 and 60, there is shown a rectal expander 410 in accordance with a further alternative embodiment of the present invention. The expander 410 is essentially similar to the expander 310 of FIGS. 52-56, except the expander includes two support arms 127, 129 extending between inflatable elements 317, 319 to provide a more uniform and flatter exposure of the rectum wall 24 in the area of opening 420 on expansion. The expander 410 is shown in the expansion position in FIGS. 61, 62, 63 and 64 which are perspective, side, plan and end views, respectively of the expander. It will also be noted that the elements 317, 319 describe the same external diameter following inflation.

Turning now to FIG. 65, there is shown a perspective view of a rectal expander 510 in accordance with a still further alternative embodiment of the present invention. The expander 510 is shown also in the side, plan and end views, respectively of FIGS. 66, 67 and 68.

The expander 510 is similar to the expander 10 of FIGS. 1-26 in that it includes expansion arms 522. These may be activated in the fashion of the expander 10, or alternatively the expanders 110, 210 described above. The expander 510 additionally includes two elongate expansion tubes 131 mounted on the expansion arms 522. The expander 510 is shown in FIGS. 65-68 following movement of the arms 522 to an expansion position and following inflation of the tubes 131.

Turning now to FIGS. 69 to 72, there are shown perspective, side, plan and end views, respectively, of an expander 610 in accordance with a still further alternative embodiment of the present invention.

The expander 610 essentially combines the features of the expander 310 of FIGS. 52-56 with the features of the expander 510 of FIGS. 65-68. The expander 610 thus comprises expansion arms 622, inflatable expansion tubes 631 and inflatable elements 617, 619. This combination provides optimum potential expansion of the rectum 12.

Figure 73:
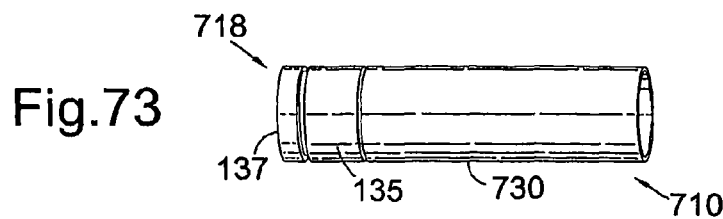
FIGS. 73-75 are perspective, side and end views of a medical apparatus in accordance with a yet further alternative embodiment of the present invention, shown in an expansion position.
Figure 74:
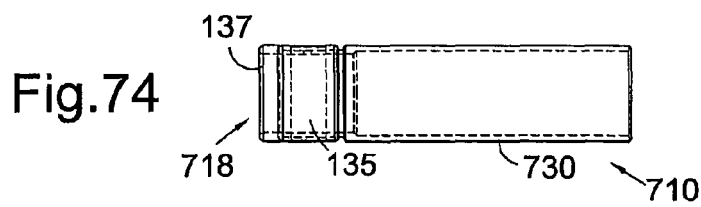
Figure 75:
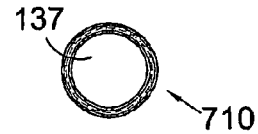
Figure 76:
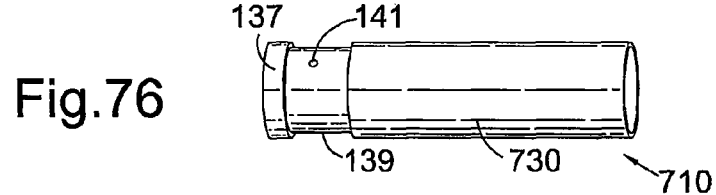
FIGS. 76-78 are perspective, side and end views of a guide member forming part of the apparatus of FIG. 73.
Figure 77:
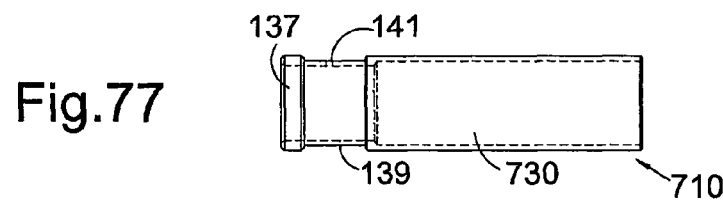
Figure 78:

Turning now to FIGS. 73-75, there are shown perspective, side and end views, respectively, of a rectal expander 710 in accordance with a yet further alternative embodiment of the present invention. The expander is shown in FIGS. 73-75 in a collapse position and includes a guide tube 730 and in inflatable element 135 mounted adjacent a leading end 718 of the tube. The leading end 718 includes an aperture 137 for access from the expander 710 into the rectum 12. The tube 730 is shown in more detail in the views of FIGS. 76-78, and it will be noted that the tube 730 includes a recess 139 for receiving the element 135 and an air hole 141 for inflation.

Figure 79:
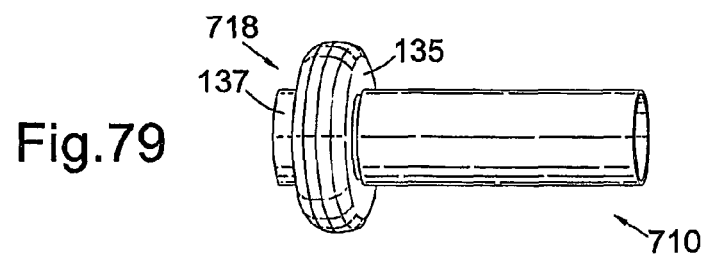
FIGS. 79-81 are perspective, side and end views, respectively, of the apparatus of FIG. 73, shown in an expansion position.
Figure 80:
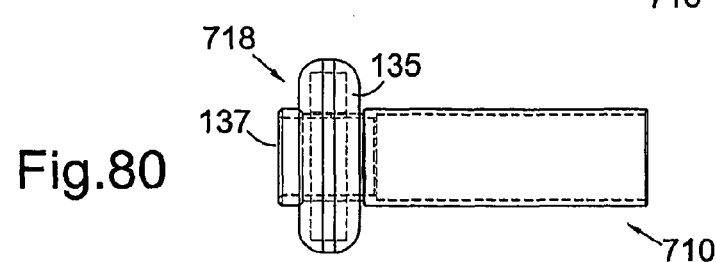
Figure 81:
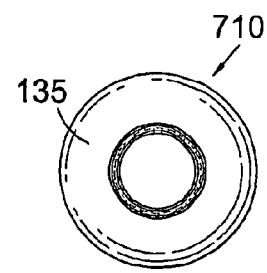

The expander 710 is shown in an expansion position in the perspective, side and end views of FIGS. 79, 80 and 81, respectively. The inflatable element 135 is expandable to a much greater external diameter than prior proposals, facilitating viewing and exposure of an area of the rectum 12 beyond the leading end 718 of the tube 730. Also, no gas insufflation of the rectum 12 is required.

Turning now to FIGS. 82 and 83, there are shown perspective and side views of an alternative expansion arm 822 which includes an arm portions 143 of greater height, to provide increased support for the rectum wall 24 on expansion. The arm portion 143 is thinner in cross-section in a recessed area 145, such that the arm is sufficiently flexible to be moved to an expansion position.

FIG. 83 is a perspective view of a further alternative arm 922 including a cut-away in arm 945 to further improve flexibility.

Various modifications may be made to the foregoing within the scope of the present invention.

For example, the medical apparatus may include a plurality of expansion arms or inflatable elements, or any desired combination thereof. The expansion arms may be of any desired material.

The collapse position of the apparatus may comprise a stressed position and the expansion position a further stressed position. In a further alternative, the collapse position may comprise a stressed position and the expansion position a rest position. Accordingly, the apparatus may be adapted to move to the expansion position in the absence of an applied collapse force.

The actuating device may comprise a mechanical, electromechanical, electrical, electronic, pneumatic or hydraulic device, or a combination thereof. Where the expansion device comprises a metal alloy or a SMA, the device may be curved/arcuate in the rest position, defining an expansion position for expanding the body passage. A force may be required to be exerted on the expansion device to move the device, and thus the apparatus, to a collapse position, for insertion and removal of the apparatus from the body passage. Where the expansion device comprises a SMA, the device may be adapted to be moved to an expansion position by heating the device above a transition temperature of the metal alloy. As will be understood by those skilled in the field of SMAs, heating of an SMA above a transition temperature causes the alloy to undergo a transition to a superelastic state, reassuming a shape in which the device was formed.

The apparatus may comprise a plurality of expansion devices and an actuation device associated with each expansion device. This may allow independent actuation of each expansion device.

The apparatus may comprise a rod or other elongate member having a leading end defining an attachment point for the expansion device. The rod may extend from a housing tube or the like, the access area extending from the leading end to the housing tube. The elongate member may be an arm, finger, leg, plate or the like, which may be arcuate in cross section, the access area defined on an underside/beneath a lower surface of the elongate member.

REFERENCES

"Technique and Results of Transanal Endoscopic Microsurgery in Early Rectal Cancer", Gerhard Buess, MD, Burkhard Mentges, MD, Klaus Manncke, MD, Michael Starlinger, MD, Horst-Dieter Becker, MD (The American Journal of Surgery, Volume 163, January 1992).

"Clinical use of a front lifting hood rectoscope tube for transanal endoscopic microsurgery", Y. Yamashita, T. Sakai, T. Maekaira, T. Shirakusa (Surgical Endoscopy, Ultrasound and Interventional Techniques, (1998) 12: 151-153)

"Rectal Expander-Assisted Transanal Endoscopic Microsurgery in rectal Tumors", Suburo Kakizoe, MD, Keiji Kakizoe, MD, Yumiko Kakizoe, MD Hiroshi Kakizoe, MD, Tamako Kakizoe, MD and Shinobu Kakizoe, MD (Surgical Laparoscopy & Edoscope (1998) Vol. 8, No. 2 pp. 117-199).

"Development of a new operating rectal tube with a side window for transanal endoscopic surgery", E. Kanehira, K. Omura, T. Kinoshita, K. Kawakami, K. Maeda and G. Watanabe (Min Invas Ther & Allied Technol 2001: 10(4/5) 243-247).

The invention claimed is:

1. A medical apparatus for location at least partly within a body passage and for expanding the body passage, the apparatus comprising:
a tubular guide member extending between a leading end and a trailing end, wherein the trailing end having an inlet providing access into the tubular guide member, the tubular guide member further having an aperture in a side wall thereof for permitting access into the body passage from the inlet at the trailing end;
a handle secured to the trailing end of the guide member;
an actuating device mounted to the handle rearwardly of the trailing end of the guide member; and
an expansion device comprising a pair of expansion arms extending along respective edge regions of the aperture, wherein one end of each arm is secured to the leading end of the guide member and an opposite end of each arm extends rearwardly of the trailing end of the guide member to engage the actuating device, wherein the arms are configured to be moved by the actuating device between a collapse position and an expansion position by controllably elastically deforming said expansion arms to expand the body passage in the region of the aperture by pushing a wall of the body passage away from the tubular guide member, the expansion arms being uninterruptedly separated by the aperture.

2. The apparatus as claimed in claim 1, wherein the apparatus is adapted to be moved between the collapse and expansion positions in incremental steps.

3. The apparatus as claimed in claim 1, wherein the apparatus is controllably movable between fully collapsed and fully expanded positions, and is adapted to be moved to a position between the fully collapsed and fully expanded positions.

4. The apparatus as claimed in claim 1, wherein the apparatus is for use in transanal endoscopic microsurgery.

5. The apparatus as claimed in claim 1, wherein the collapse position of the apparatus is a rest position and the expansion position is a stressed position, and wherein the apparatus is adapted to move to the collapse position in the absence of an applied expansion force.

6. The apparatus as claimed in claim 1, wherein the collapse position of the apparatus is a first stressed position and the expansion position is a further stressed position, and wherein the apparatus is adapted to move to the first stressed position in the absence of an applied expansion force.

7. The apparatus as claimed in claim 1, wherein the collapse position of the apparatus is a stressed position and the expansion position is a rest position, and wherein the apparatus is adapted to move to the expansion position in the absence of an applied collapse force.

8. The apparatus as claimed in claim 1, wherein the actuating device comprises an activating member adapted for moving the apparatus between the collapse and expansion positions.

9. The apparatus as claimed in claim 8, wherein the activating member is moveable relative to a remainder of the apparatus.

10. The apparatus as claimed in claim 9, wherein the actuating device comprises a screw mechanism including a screw threaded member coupled to the activating member, rotation of the screw threaded member adapted to move the activating member relative to the remainder of the apparatus, thereby moving the apparatus between the collapse and expansion positions.

11. The apparatus as claimed in claim 9, wherein the actuating device comprises a ratchet mechanism including a slider coupled to the activating member and a locking member, movement of the slider relative to the locking member adapted to move the activating member relative to the remainder of the apparatus, thereby moving the apparatus between the collapse and expansion positions.

12. The apparatus as claimed in claim 8, wherein the actuating device comprises a motor for moving the activating member.

13. The apparatus as claimed in claim 8, wherein the expansion device is movable to the expansion position in response to a force applied by the actuating device.

14. The apparatus as claimed in claim 8, wherein the expansion device is configured to move the expansion arms simultaneously.

15. The apparatus as claimed in claim 1, further comprising a lock for locking the apparatus in a desired position.

16. The apparatus as claimed in claim 1, wherein the aperture extends from the leading end and part way along a length of the apparatus.

17. The apparatus as claimed in claim 1, wherein a distance between the access area and a trailing end of the guide member facilitates access through the opening.

18. The apparatus as claimed in claim 1, wherein the aperture is an elongate opening, of a greater dimension in a direction along a main axis of the guide member than in a direction around a perimeter of the guide member.

19. The apparatus as claimed in claim 1, wherein the aperture is an opening extending around at least half of a perimeter of the guide member.

20. The apparatus as claimed in claim 1, wherein the pair of expansion arms are mounted on and extend longitudinally with respect to the guide member.

21. The apparatus as claimed in claim 1, wherein each of the pair of expansion arms is adapted to adopt a curved shape when in an expansion position.

22. The apparatus as claimed in claim 1, wherein the pair of expansion arms are made of a shape memory alloy.

23. The apparatus as claimed in claim 22, wherein the expansion arm is adapted to be moved to the expansion position by heating the device above a transition temperature of the shape memory alloy.

24. The apparatus as claimed in claim 1, wherein the expansion device comprises a plurality of inflatable elements, the elements axially spaced with respect to a main axis of the apparatus.

25. The apparatus as claimed in claim 1, further comprising a flexible cover extending between the expansion device and the guide member, for preventing any part of the body passage from damage during movement of the expansion device between the collapse and expansion positions.

26. The apparatus as claimed in claim 1, wherein the expansion device provides a force-feedback to an operator during movement between the collapse and expansion positions.

27. The apparatus as claimed in claim 1, further comprising a device for measuring an expansion force exerted on the body passage during movement of the apparatus between the collapse and expansion positions.

28. A method of providing access to a body passage, the method comprising the steps of:
  inserting a medical apparatus having:
    a tubular guide member extending between a leading end and a trailing end, wherein the trailing end has an inlet providing access into the tubular guide member, the tubular guide member also having an aperture in a side wall thereof for permitting access into the body passage from the inlet at the trailing end;
    a handle secured to the trailing end of the guide member;
    an actuating device mounted to the handle rearwardly of the trailing end of the guide member;
    an expansion device comprising a pair of expansion arms extending along respective edge regions of the aperture, wherein one end of each arm is secured to the leading end of the guide member and an opposite end of each arm extends rearwardly of the trailing end of the guide member to engage the actuating device, wherein the arms are configured to be moved by the actuating device between a collapse position and an expansion position by controllably elastically deforming said expansion arms to expand the body passage in the region of the aperture, the expansion arms being uninterruptedly separated by the aperture;
  controllably moving the medical apparatus from the collapse position to an expansion position by controllably elastically deforming the pair of expansion arms to expand the body passage in the region of the aperture by pushing a wall of the body passage away from the tubular guide member; and
  accessing the body passage through at least part of the aperture spaced from the leading end of the apparatus.

29. The method as claimed in claim 28, further comprising the step of exerting an expansion force on the medical apparatus following insertion into the body passage, to move the expansion arms to the expansion position.

30. The method as claimed in claim 28, further comprising the steps of exerting a collapse force on the medical apparatus, to move the expansion arms to the collapse position and to restrain the expansion arms in the collapse position for insertion of the medical apparatus into the body passage, and subsequently releasing the collapse force, whereupon the expansion arms move to the expansion position.

31. The method as claimed in claim 28, further comprising the steps of controllably moving the expansion arms from the expansion position to the collapse position and removing the medical apparatus from the body passage.

32. The method as claimed in claim 31, further comprising the steps of rotating the medical apparatus relative to the body passage, reinserting the medical apparatus into the body passage and returning the expansion arms to the expansion position.

33. The method as claimed in claim 28, further comprising the steps of returning the expansion arms to the collapse position, rotating the medical apparatus within the body passage, and then returning the expansion arms to the expansion position.

34. The method as claimed in claim 28, further comprising the step of viewing the body passage through the aperture.

35. The method as claimed in claim 28, further comprising the step of conducting a diagnostic procedure on the body passage.

* * * * *